(12) United States Patent
Wakefield

(10) Patent No.: US 9,382,534 B2
(45) Date of Patent: Jul. 5, 2016

(54) OPTIMIZATION OF VECTORS FOR EFFECTIVE DELIVERY AND EXPRESSION OF GENETIC CONTENT

(71) Applicant: John Wakefield, Birmingham, AL (US)

(72) Inventor: John Wakefield, Birmingham, AL (US)

(73) Assignee: GE Healthcare Dharmacon, Inc., Lafayette, CO (US)

( * ) Notice: Subject to any disclaimer, the term of this patent is extended or adjusted under 35 U.S.C. 154(b) by 2 days.

(21) Appl. No.: 14/238,870

(22) PCT Filed: Oct. 2, 2012

(86) PCT No.: PCT/US2012/058384
§ 371 (c)(1),
(2) Date: Feb. 14, 2014

(87) PCT Pub. No.: WO2013/052432
PCT Pub. Date: Apr. 11, 2013

(65) Prior Publication Data
US 2014/0213639 A1    Jul. 31, 2014

Related U.S. Application Data

(60) Provisional application No. 61/543,596, filed on Oct. 5, 2011.

(51) Int. Cl.
| | | |
|---|---|---|
| *C12N 15/00* | (2006.01) | |
| *C12Q 1/68* | (2006.01) | |
| *C12N 15/10* | (2006.01) | |
| *C12N 15/11* | (2006.01) | |
| *C12N 5/00* | (2006.01) | |

(52) U.S. Cl.
CPC .......... *C12N 15/1086* (2013.01); *C12N 15/111* (2013.01); *C12N 2330/51* (2013.01); *C12N 2740/16043* (2013.01)

(58) Field of Classification Search
None
See application file for complete search history.

(56) References Cited

U.S. PATENT DOCUMENTS

| | | |
|---|---|---|
| 7,090,837 B2 | 8/2006 | Spencer et al. |
| 7,323,619 B2 | 1/2008 | Baltimore et al. |
| 7,915,000 B2 | 3/2011 | Bowdish et al. |
| 2005/0003547 A1 | 1/2005 | Spencer et al. |
| 2007/0161031 A1 | 7/2007 | Trinklein et al. |
| 2008/0120732 A1 | 5/2008 | Elliot |
| 2009/0130751 A1 | 5/2009 | Davidson et al. |
| 2009/0142839 A1 | 6/2009 | Primiano |
| 2010/0172871 A1 | 7/2010 | Flannery et al. |
| 2010/0256222 A1 | 10/2010 | Kelley et al. |

OTHER PUBLICATIONS

European Patent Office, Supplementary European Search Report, EP 12839041, May 5, 2015.
Stegmeier Frank et al, "A lentiviral microRNA-based system for single-copy polymerase II-regulated RNA interference in mammalian cells", Proceedings of the National Academy of Sciences, National Academy of Sciences, US, vol. 102, No. 37, Sep. 1, 2005.
Scott F. Geller et al, "In vitro analysis of promoter activity in Muller cells", Molecular Vision, Molecular Vision, SN, Atlanta, vol. 14, Apr. 23, 2008.
Rubinson D A et al, "A lentivirus-based system to functionally silence genes in primary mammalian cells, stem cells and transgenic mice by RNA interference", Nature Genetics, Nature Publishing Group, New York, US, vol. 33, 1, Mar. 2003.
Cockrell Adam S et al, "Gene delivery by lentivirus vectors", Molecular Biotechnology, vol. 36, No. 3, Jul. 2007.
International Search Report and Written Opinion, PCT/US12/58384, dated Feb. 3, 2013.
Qin, Jane Yuxia, Systematic Comparison of Constitutive Promoters and the Doxycycline-Inducible Promoter, PLoS ONE, May 2010, vol. 5, Issue 5, pp. 1-4.
PCT International Preliminary Report on Patentability, The International Bureau of WIPO, Apr. 8, 2014, PCT/US2012/058384.

*Primary Examiner* — Sean McGarry
(74) *Attorney, Agent, or Firm* — Dorf & Nelson LLP; Scott D. Locke, Esq.

(57) ABSTRACT

Lentiviral vectors, plates, kits and methods are provided that permit improved efficiency for selection of a promoter sequence for use in a lentiviral application. Through various embodiments of the present invention, a researcher may first evaluate and then choose in a modular fashion, a vector comprising a promoter that is effective for expression in a particular cell line or type.

15 Claims, 12 Drawing Sheets

SEQUENCE LISTING

<160> NUMBER OF SEQ ID NOS: 7

<210> SEQ ID NO 1
<211> LENGTH: 581
<212> TYPE: DNA
<213> ORGANISM: human cytomegalovirus

<400> SEQUENCE: 1

```
aatagtaatc aattacgggg tcattagttc atagcccata tatggagttc cgcgttacat      60
aacttacggt aaatggcccg cctggctgac cgcccaacga cccccgccca ttgacgtcaa     120
taatgacgta tgttcccata gtaacgccaa tagggacttt ccattgacgt caatgggtgg     180
agtatttacg gtaaactgcc cacttggcag tacatcaagt gtatcatatg ccaagtacgc     240
cccctattga cgtcaatgac ggtaaatggc ccgcctggca ttatgcccag tacatgacct     300
tatgggactt tcctacttgg cagtacatct acgtattagt catcgctatt accatggtga     360
tgcggttttg gcagtacatc aatgggcgtg gatagcggtt tgactcacgg ggatttccaa     420
gtctccaccc cattgacgtc aatgggagtt tgttttggca ccaaaatcaa cgggactttc     480
caaaatgtcg taacaactcc gccccattga cgcaaatggg cggtaggcgt gtacggtggg     540
aggtctatat aagcagagct cgtttagtga accgtcagat c                        581
```

<210> SEQ ID NO 2
<211> LENGTH: 537
<212> TYPE: DNA
<213> ORGANISM: mouse cytomegalovirus

<400> SEQUENCE: 2

```
tggcacgtat actgagtcat tagggacttt ccaatggggtt ttgcccagta cataaggtca     60
atagggggtga atcaacagga aagtcccatt ggagccaagt acactgagtc aataggggact    120
ttccattggg ttttgcccag tacaaaaggt caatagggggg tgagtcaatg gttttttccc    180
attattggca cgtacataag gtcaataggg gtgagtcatt gggttttttcc agccaattta    240
attaaaacgc catgtacttt cccaccattg acgtcaatgg gctattgaaa ctaatgcaac    300
gtgacccttta aacggtactt tcccatagct gattaatggg aaagtaccgt tctcagagcc    360
aatacacgtc aatgggaagt gaaagggcag ccaaaacgta acaccgcccc ggttttcccc    420
tggaaattcc atattggcac gcattctatt ggctgagctg cgttctacgt gggtataaga    480
ggcgcgacca gcgtcggtac cgtcgcagtc ttcggtctga ccaccgtaga acgcaga        537
```

<210> SEQ ID NO 3
<211> LENGTH: 1118
<212> TYPE: DNA
<213> ORGANISM: Homo sapiens

<400> SEQUENCE: 3

```
tccccgagaa gttgggggga ggggtcggca attgaaccgg tgcctagaga aggtggcgcg      60
gggtaaactg ggaaagtgat gtcgtgtact ggctccgcct ttttcccgag ggtgggggag     120
aaccgtatat aagtgcagta gtcgccgtga acgttctttt tcgcaacggg tttgccgcca     180
gaacacaggt aagtgccgtg tgtggttccc gcgggcctgg cctctttacg ggttatggcc     240
cttgcgtgcc ttgaattact tccacctggc tccagtacgt gattcttgat cccgagctgg     300
agccaggggc gggccttgcg ctttaggagc ccttcgcct cgtgcttgag ttgaggcctg      360
gcctgggcgc tggggccgcc gcgtgcgaat ctggtggcac cttcgcgcct gtctcgctgc     420
tttcgataag tctctagcca tttaaaattt ttgatgacct gctgcgacgc tttttttctg     480
```

```
gcaagatagt cttgtaaatg cgggccagga tctgcacact ggtatttcgg ttttgggc       540 cgcgggcggc gacggggccc gtgcgtccca gcgcacatgt tcggcgaggc ggggcctgcg     600
agcgcggcca ccgagaatcg gacggggta gtctcaagct ggccggcctg ctctggtgcc     660
tggcctcgcg ccgccgtgta tcgccccgcc ctgggcggca aggctgggcc ggtcggcacc    720
agttgcgtga gcggaaagat ggccgcttcc cggccctgct ccagggggct caaaatggag    780
gacgcggcgc tcgggagagc gggcgggtga gtcacccaca caaggaaag gggccttcc      840 gtcctcagcc gtcgcttcat gtgactccac ggagtaccgg gcgccgtcca ggcacctcga    900
ttagttctgg agcttttgga gtacgtcgtc tttaggttgg ggggaggggt tttatgcgat    960
ggagtttccc cacactgagt gggtggagac tgaagttagg ccagcttggc acttgatgta    1020
attctccttg gaattttgccc ttttttgagtt tggatcttgg ttcattctca agcctcagac  1080
agtggttcaa agttttttc ttccatttca ggtgtcgt                             1118

<210> SEQ ID NO 4
<211> LENGTH: 1348
<212> TYPE: DNA
<213> ORGANISM: Mus musculus

<400> SEQUENCE: 4
agagtaattc atacaaaagg agggatcgcc ttcgcctggg gaagtcccag ggaccgtcgc     60
taaattctca taacccataa tcccggtacc cgccccacca cagtgcgagg agcatgcgct    120
cagggctgag cgcggggaga gcagagcaca caagctcata gaccctggtc gtggggggag    180 ggcgcactg agcgggggggg gggggggtga tgggggggag gaccggggag ctggcgcggg    240
gcaaactggg aaagcggtgt cgtgtgctgg ctccgccctc ttcccgaggg tgggggagaa    300
cggtatataa gtgcggcagt cgccttggac gttctttttc gcaacgggtt tgccgtcaga    360
acgcaggtga ggggcgggtg tggcttccgc gggccgccga gctggaggtc ctgctccgag    420
cgggccgggc cccgctgtcg tcggcgggga ttagctgcga gcattcccgc ttcgagttgc    480
gggcggcgcg ggaggcagag tgcgaggcct agcggcaacc ccgtagcctc gcctcgtgtc    540
cggcttgagg cctagcgtgg tgtccgcgcc gccgccgcgt gctactccgg ccgcactctg    600 gtctttttt ttttgttgtt gttgttgccc tgctgccttc gattgccgtt cagcaatagg     660
ggctaacaaa gggagggtgc ggggcttgct cgcccggagc ccggagaggt catggttggg    720
gaggaatgga gggacaggag tggcggctgg ggcccgcccg ccttcggagc acatgtccga    780
cgccacctgg atggggcgag gcctgggggtt ttttcccgaag caaccaggct ggggttagcg   840
tgccgaggcc atgtggcccc agcacccggc acgatctggc ttggcggcgc cgcgttgccc    900
tgcctcccta actagggtga ggccatcccg tccggcacca gttgcgtgcg tggaaagatg    960
gccgctcccg ggccctgttg caaggagctc aaaatggagg acgcggcagc ccggtggagc    1020
gggcgggtga gtcacccaca caaggaaga gggcctggtc cctcaccggc tgctgcttcc     1080
tgtgaccccg tggtcctatc ggccgcaata gtcacctcgg gcttttgagc acggctagtc    1140
gcggcggggg gagggggatgt aatggcgttg gagtttgttc acatttggtg ggtggagact   1200
agtcaggcca gcctggcgct ggaagtcatt tttggaattt gtcccccttga gttttgagcg   1260 gagctaattc tcgggcttct tagcggttca aaggtatctt ttaaaccctt ttttaggtgt    1320
tgtgaaaacc accgctaatt caaagcaa                                       1348

<210> SEQ ID NO 5
```

<211> LENGTH: 1737
<212> TYPE: DNA
<213> ORGANISM: Artificial Sequence
<220> FEATURE:
<223> OTHER INFORMATION: a combination of the cytomegalovirus early
      enhancer element and chicken beta-actin promoter

<400> SEQUENCE: 5

```
gacattgatt attgactagt tattaatagt aatcaattac ggggtcatta gttcatagcc     60
catatatgga gttccgcgtt acataactta cggtaaatgg cccgcctggc tgaccgccca    120
acgacccccg cccattgacg tcaataatga cgtatgttcc catagtaacg ccaataggga    180
ctttccattg acgtcaatgg gtggactatt tacggtaaac tgcccacttg gcagtacatc    240
aagtgtatca tatgccaagt acgccccta ttgacgtcaa tgacggtaaa tggcccgcct    300
ggcattatgc ccagtacatg accttatggg actttcctac ttggcagtac atctacgtat    360
tagtcatcgc tattaccatg gtcgaggtg agccccacgt tctgcttcac tctccccatc    420
tccccccct cccacccccc aattttgtat ttatttattt tttaattatt ttgtgcagcg    480
atggggcgg ggggggggg ggcgcgcgcc aggcggggcg gggcggggcg aggggcgggg    540
cggggcgagg cggagaggtg cggcggcagc caatcagagc ggcgcgctcc gaaagtttcc    600
ttttatggcg aggcggcggc ggcggcggcc ctataaaaag cgaagcgcgc ggcgggcggg    660
agtcgctgcg ttgccttcgc cccgtgcccc gctccgcgcc gcctcgcgcc gcccgccccg    720
gctctgactg accgcgttac tcccacaggt gagcgggcgg gacggcccct tctcctccggg    780
ctgtaattag cgcttggttt aatgacggct cgtttctttt ctgtggctgc gtgaaagcct    840
taaagggctc cggagggcc ctttgtgcgg ggggagcgg ctcgggggt gcgtgcgtgt    900
gtgtgtgcgt ggggagcgcc gcgtgcggcc cgcgctgccc ggcggctgtg agcgctgcgg    960
gcgcggcgcg gggctttgtg cgctccgcgt gtgcgcgagg ggagcgcggc cggggcggt   1020
gccccgcgt gcggggggc tgcgagggga acaaaggctg cgtgcggggt gtgtgcgtgg   1080
ggggtgagc aggggtgtg ggcgcggcgg tcgggctgta accccccct gcacccccct   1140
ccccgagttg ctgagcacgg cccggcttcg ggtgcggggc tccgtgcggg gcgtggcgcg   1200
gggctcgccg tgccgggcgg ggggtggcgg caggtggggg tgccgggcgg ggcggggccg   1260
cctcgggccg ggagggctc ggggagggg cgcggcggcc ccggagcgcc ggcggctgtc   1320
gaggcgcggc gagccgcagc cattgccttt tatggtaatc gtgcgagagg gcgcagggac   1380
ttcctttgtc ccaaatctgg cggagccgaa atctgggagg cgccgccgca cccctctag   1440
cgggcgcggg cgaagcggtg cggcgccggc aggaaggaaa tgggcgggga gggccttcgt   1500
gcgtcgccgc gccgccgtcc ccttctccat ctccagcctc ggggctgccg caggggacg   1560
gctgccttcg gggggacgg gcagggcgg ggttcggctt ctggcgtgtg accgcggct   1620
ctagagcctc tgctaaccat gttcatgcct tcttcttttt cctacagctc ctgggcaacg   1680
tgctggttgt tgtgctgtct catcattttg gcaaagaatt cccgccgcc accatgg     1737
```

<210> SEQ ID NO 6
<211> LENGTH: 524
<212> TYPE: DNA
<213> ORGANISM: Mus musculus

<400> SEQUENCE: 6

```
caattctacc gggtagggga ggcgcttttc ccaaggcagt ctggagcatg cgctttagca     60
gccccgctgg gcacttggcg ctacacaagt ggcctctggc ctcgcacaca ttccacatcc    120
```

```
-continued accggtaggc gccaaccggc tccgttctttt ggtggcccct tcgcgccacc ttctactcct      180
cccctagtca ggaagttccc ccccgccccg cagctcgcgt cgtgcaggac gtgacaaatg      240
gaagtagcac gtctcactag tctcgtgcag atggacagca ccgctgagca atggaagcgg      300
gtaggccttt ggggcagcgg ccaatagcag ctttgctcct tcgctttctg ggctcagagg      360
ctgggaaggg gtgggtccgg gggcgggctc agggggcgggc tcagggggcgg ggcgggcgcc      420 cgaaggtcct ccggaggccc ggcattctgc acgcttcaaa agcgcacgtc tgccgcgctg      480
ttctcctctt cctcatctcc gggcctttcg acctgcagcc caag                       524

<210> SEQ ID NO 7
<211> LENGTH: 1212
<212> TYPE: DNA
<213> ORGANISM: Homo sapiens

<400> SEQUENCE: 7
ggcctccgcg ccgggttttg gcgcctcccg cgggcgcccc cctcctcacg gcgagcgctg       60
ccacgtcaga cgaagggcgc agcgagcgtc ctgatccttc cgcccggacg ctcaggacag      120
cggcccgctg ctcataagac tcggccttag aaccccagta tcagcagaag gacattttag      180
gacgggactt gggtgactct agggcactgg ttttctttcc agagagcgga acaggcgagg      240
aaaagtagtc ccttctcggc gattctgcgg agggatctcc gtgggcggt gaacgccgat       300 gattatataa ggacgcgccg ggtgtggcac agctagttcc gtcgcagccg ggatttgggt      360
cgcggttctt gtttgtggat cgctgtgatc gtcacttggt gagtagcggg ctgctgggct      420
ggccggggct ttcgtggccg ccgggccgct cggtgggacg gaagcgtgtg gagagaccgc      480
caagggctgt agtctgggtc cgcgagcaag gttgccctga actgggggtt gggggagcg       540 cagcaaaatg gcggctgttc ccgagtcttg aatggaagac gcttgtgagg cgggctgtga      600
ggtcgttgaa acaaggtggg gggcatggtg ggcggcaaga acccaaggtc ttgaggcctt      660
cgctaatgcg ggaaagctct tattcgggtg agatgggctg gggcaccatc tggggaccct      720
gacgtgaagt ttgtcactga ctggagaact cggtttgtcg tctgttgcgg gggcggcagt      780
tatggcggtg ccgttgggca gtgcacccgt acctttggga gcgcgcgccc tcgtcgtgtc      840
gtgacgtcac ccgttctgtt ggcttataat gcagggtggg gccacctgcc ggtaggtgtg      900
cggtaggctt ttctccgtcg caggacgcag ggttcgggcc tagggtaggc tctcctgaat      960
cgacaggcgc cggacctctg gtgaggggag ggataagtga ggcgtcagtt tctttggtcg     1020
gttttatgta cctatcttct taagtagctg aagctccggt tttgaactat gcgctcgggg     1080
ttggcgagtg tgttttgtga agttttttag gcacccttttg aaatgtaatc atttgggtca     1140
atatgtaatt ttcagtgtta gactagtaaa ttgtccgcta aattctggcc gttttttggct     1200 tttttgttag ac                                                         1212
```

OPTIMIZATION OF VECTORS FOR EFFECTIVE DELIVERY AND EXPRESSION OF GENETIC CONTENT

FIELD OF INVENTION

The present invention relates to lentiviruses.

BACKGROUND OF THE INVENTION

Gene therapy approaches rely on the efficient transfer of genes to the desired target cells. In order to increase efficiency, researchers have explored ways to use both viral and non-viral vectors.

One of the areas that researchers have explored with great interest is the use of lentiviral vectors. Lentiviral vectors make use of lentiviral polynucleotide sequences and are a subclass of retroviral vectors. However, unlike other retroviruses, lentiviruses are able to integrate into the genome of non-dividing cells. After entry into a cell, the viral genome, which is in the form of single-stranded RNA, is reverse transcribed to generate a double-stranded DNA, which is then inserted into the host genome. Because lentiviral vectors can cause their sequences to be integrated into non-dividing cells, they provide particularly promising leads for gene therapy.

Another area of interest for researchers is RNA inference, also referred to as RNAi, which involves the phenomenon of gene silencing following the introduction of double-stranded RNA (dsRNA) into cells. In mammalian cells, in order to avoid an interferon response, RNAi is conducted by using short interfering RNA, also known as siRNA, which may comprise two separate strands of RNA or a hairpin structures also known as shRNA, that may be processed by a cell into a short duplex that contains two different strands.

Lentiviruses have recently been viewed and tried as potential means of efficiently introducing shRNA into cells. When introduced into cells under conditions that permit the lentiviruses to act in their intended manners, these vectors have demonstrated the potential to be important tools for gene therapy.

As persons of ordinary skill in the art will recognize, lentiviruses, like other vectors, are often created and introduced into cells with internal promoter regions, which serve the function of providing control points for transcription. However, promoter activity can vary widely across cell lines and cell types. Inefficient promoter activity can result in poor expression, which can often be misinterpreted as unsuccessful delivery, unsuccessful genomic integration or in the case of shRNA-containing vectors, poor gene silencing efficiency.

Thus, there is a need to provide better options for permitting persons of ordinary skill in the art to select elements of their lentiviral vector constructs with greater likelihood that the constructs will effectively introduce the desired genetic element into any cell or organism and express the desired genetic elements in the cell or organism.

SUMMARY OF THE INVENTION

The present invention is directed to plates, kits, methods, and vectors that facilitate the design of efficient genetic constructs and the use of these constructs. Through various embodiments of the present invention, there is an ability to assess promoter activity in cells of interest prior to conducting a gene silencing or expression experiment of therapy. Advantageously, some of these embodiments can provide cost-effective strategies for the biotechnology industry to select promoters and other modular elements or a suppression vector, particularly when conducting in vivo experiments that use expensive animal models or other experiments that use primary cells that are difficult to isolate.

According to a first embodiment, the present invention provides a plate for selection of a promoter sequence, wherein the plate comprises a first row of a plurality of loci and a second row of a plurality of loci, wherein each of the plurality of loci within the first row comprises a first lentiviral vector comprising: (a) a promoter sequence, e.g., a promoter sequence selected from the group consisting of sequences for human cytomegalovirus (hCMV), mouse cytomegalovirus (mCMV), human elongation factor 1 alpha (hEF1α), mouse elongation factor 1 alpha (mEF1α), CAG (a combination of the cytomegalovirus (CMV) early enhancer element and chicken beta-actin promoter), human phosphoglycerate kinase (hPGK), mouse phosphoglycerate kinase (mPGK), and human ubiquitin (UBC); and (b) optionally, a reporter sequence. In some embodiments, the lentiviral vector may further comprise one or more if not all of: (c) a scaffolding sequence such as a miRNA scaffolding sequence, wherein the miRNA scaffolding sequence is derived from an endogenous pri-miRNA sequence; (d) a mature strand insert sequence; and (e) a star strand insert sequence. In some embodiments, the mature strand insert sequence and the star strand insert sequence are each 18-30 nucleotides in length, the mature strand insert sequence and the star strand insert sequence are each located within an miRNA scaffolding sequence and the mature strand insert sequence is at least 60% complementary to the star strand insert sequence. Further, in some embodiments, neither the mature strand insert sequence nor the star strand insert sequence comprise a sequence derived from an endogenous miRNA that comprises the pri-miRNA scaffolding; and each of the plurality of loci within the second row comprises a second lentiviral vector, wherein the second lentiviral vector is the same as the first lentiviral vector except that it comprises a different promoter sequence than in the first row, for example a different promoter sequence selected from the group consisting of sequences for hCMV, mCMV, hEF1α, mEF1α, CAG, hPGK, mPGK, and UBC.

According to a second embodiment, the present invention provides a plate for selection of a promoter sequence, wherein the plate comprises a first row of a plurality of loci and a second row of a plurality of loci, wherein each of the plurality of loci within the first row comprises a first lentiviral vector comprising: (a) a promoter sequence, e.g., a promoter sequence selected from the group consisting of sequences for human cytomegalovirus (hCMV), mouse cytomegalovirus (mCMV), human elongation factor 1 alpha (hEF1α), mouse elongation factor 1 alpha (mEF1α), CAG (a combination of the cytomegalovirus (CMV) early enhancer element and chicken beta-actin promoter), mouse phosphoglycerate kinase (mPGK), and human ubiquitin (UBC); and (b) optionally, a reporter sequence. In some embodiments, the lentiviral vector may further comprise one or more if not all of: (c) a scaffolding sequence such as a miRNA scaffolding sequence, wherein the miRNA scaffolding sequence is derived from an endogenous pri-miRNA sequence; (d) a mature strand insert sequence; and (e) a star strand insert sequence. In some embodiments, the mature strand insert sequence and the star strand insert sequence are each 18-30 nucleotides in length, the mature strand insert sequence and the star strand insert sequence are each located within an miRNA scaffolding sequence and the mature strand insert sequence is at least 60% complementary to the star strand insert sequence. Further, in some embodiments, neither the mature strand insert sequence nor the star strand insert sequence comprise a sequence derived from an endogenous miRNA that comprises the primiRNA scaffolding; and each of the plurality of loci within the second row comprises a second lentiviral vector, wherein the second lentiviral vector is the same as the first lentiviral vector except that it comprises a different promoter sequence than in the first row, for example a different promoter sequence selected from the group consisting of sequences for hCMV, mCMV, hEF1α, mEF1α, CAG, mPGK, and UBC.

According to a third embodiment, the present invention provides a method for selecting and obtaining a suppression vector. For convenience and unless otherwise specified, the phrase "suppression vector" may be used herein to refer to the vector that is designed to include a promoter that is selected through embodiments of the present invention. A suppression vector may be a lentiviral vector, but it may also be other types of expression vectors such as phages, plasmids or cosmids. In some embodiments, the expression vector comprises an RNA sequence such as ORF, shRNA or microRNA.

Some methods of the present invention comprise: (a) transducing different cells from a cell line of interest with lentiviral vectors located at at least two different loci of a plate described herein; (b) measuring intensities of signals generated by activity in the cells, thereby establishing a plurality of measured intensities; (c) selecting a promoter sequence for insertion into a suppression vector, thereby obtaining a selected promoter sequence, wherein the selected promoter sequence has the highest measured intensity at the lowest multiplicity of infection; and (d) obtaining a suppression vector. The method may also require that the highest measured intensity is greater than a predefined level, such as being measurable by a device or visible to the human eye. The suppression vector may comprise (i) the selected promoter sequence; (ii) optionally, a reporter sequence; (iii) an miRNA scaffolding sequence, wherein the miRNA scaffolding sequence is derived from an endogenous pri-miRNA sequence; (iv) a mature strand insert sequence; and (v) a star strand insert sequence, wherein the mature strand insert sequence and the star strand insert sequence are each 18-30 or 18-23 or 19-23 nucleotides in length, the mature strand insert sequence and the star strand insert sequence are each located within the miRNA scaffolding sequence and the mature strand insert sequence is at least 60% complementary to the star strand insert sequence, and neither the mature strand insert sequence nor the star strand insert sequence comprise a sequence derived from the endogenous pri-miRNA.

As noted above, the suppression vector, may for example, comprise the promoter that is selected in step (c). It also may comprise a scaffolding sequence that is the same as a scaffolding sequence within the lentiviral vectors of step (a). Alternatively, the suppression vector may contain a different scaffolding or no scaffolding. Moreover, in some embodiments, the lentiviral vector contains a non-targeting control sequence, but the suppression vector comprises a sequence designed to target or silence a nucleotide sequence within a cell or organism. The suppression vectors may then be used to introduce genetic material into cells in vitro or into an organism in vivo.

According to a fourth embodiment, the present invention provides a lentiviral vector comprising: (a) a promoter sequence selected from the group consisting of sequences for hCMV, mCMV, hEF1α, mEF1α, CAG, hPGK, mPGK, and UBC; and (b) a reporter sequence. The lentiviral vector may further comprise one or more of a scaffolding sequence, a mature strand insert sequence and a star strand insert sequence. Optionally, within the lentiviral vector, the promoter sequence may be selected from the group consisting of sequences for hCMV, mCMV, hEF1α, mEF1α, CAG, mPGK, and UBC According to a fifth embodiment, the present invention provides a lentiviral vector comprising: (a) a promoter sequence selected from the group consisting of sequences for hCMV, mCMV, hEF1α, mEF1α, CAG, hPGK, mPGK, and UBC; (b) optionally, a reporter sequence; (c) an miRNA scaffolding sequence, wherein the miRNA scaffolding sequence is derived from an endogenous pri-miRNA sequence; (d) a mature strand insert sequence; and (e) a star strand insert sequence, wherein the mature strand insert sequence and the star strand insert sequence are each 18-23 nucleotides in length, and the mature strand insert sequence and the star strand insert sequence are each located within the miRNA scaffolding and the mature strand insert sequence is at least 60% complementary to the star strand insert sequence, and neither the mature strand insert sequence nor the star strand insert sequence comprise a sequence derived from the endogenous pri-miRNA. Optionally, within the lentiviral vector, the promoter sequence may be selected from the group consisting of sequences for hCMV, mCMV, hEF1α, mEF1α, CAG, mPGK, and UBC.

According to a sixth embodiment, the present invention provides a kit for suppressing gene expression comprising a plurality of lentiviral vectors described herein, wherein the plurality of lentiviral vectors comprises at least two lentiviral vectors that have different promoter sequences. Preferably, although having different promoter sequences they otherwise have the same sequences.

According to a seventh embodiment, the present invention provides a plate for selection of a promoter sequence, wherein the plate comprises a first row of a plurality of loci and a second row of a plurality of loci, wherein each of at least two of the plurality of loci within the first row comprises a first lentiviral vector comprising: (i) a first promoter sequence; and (ii) a reporter sequence; and at least two of the plurality of loci within the second row each comprises a second lentiviral vector, wherein the second lentiviral vector is the same as the first lentiviral vector except that it does not comprise the first promoter sequence and comprises a second promoter sequence that is different from the first promoter sequence.

The plates and various other embodiments of the present invention may be advantageous for use by researchers who do not necessarily have a priori knowledge of optimal promoters for their biological cells or animal models of interest because they offer cost-effective means by which to design lentiviral particles. Thus, through the use of one or more of the embodiments of the present invention, one may achieve one or more of the following advantages: increased efficiency when testing promoters; increased efficiency when choosing reporters; increased efficiency of transduction; and an improved ability to develop and to use customized vectors that have a likelihood of success.

DETAILED DESCRIPTION

Figure 1:
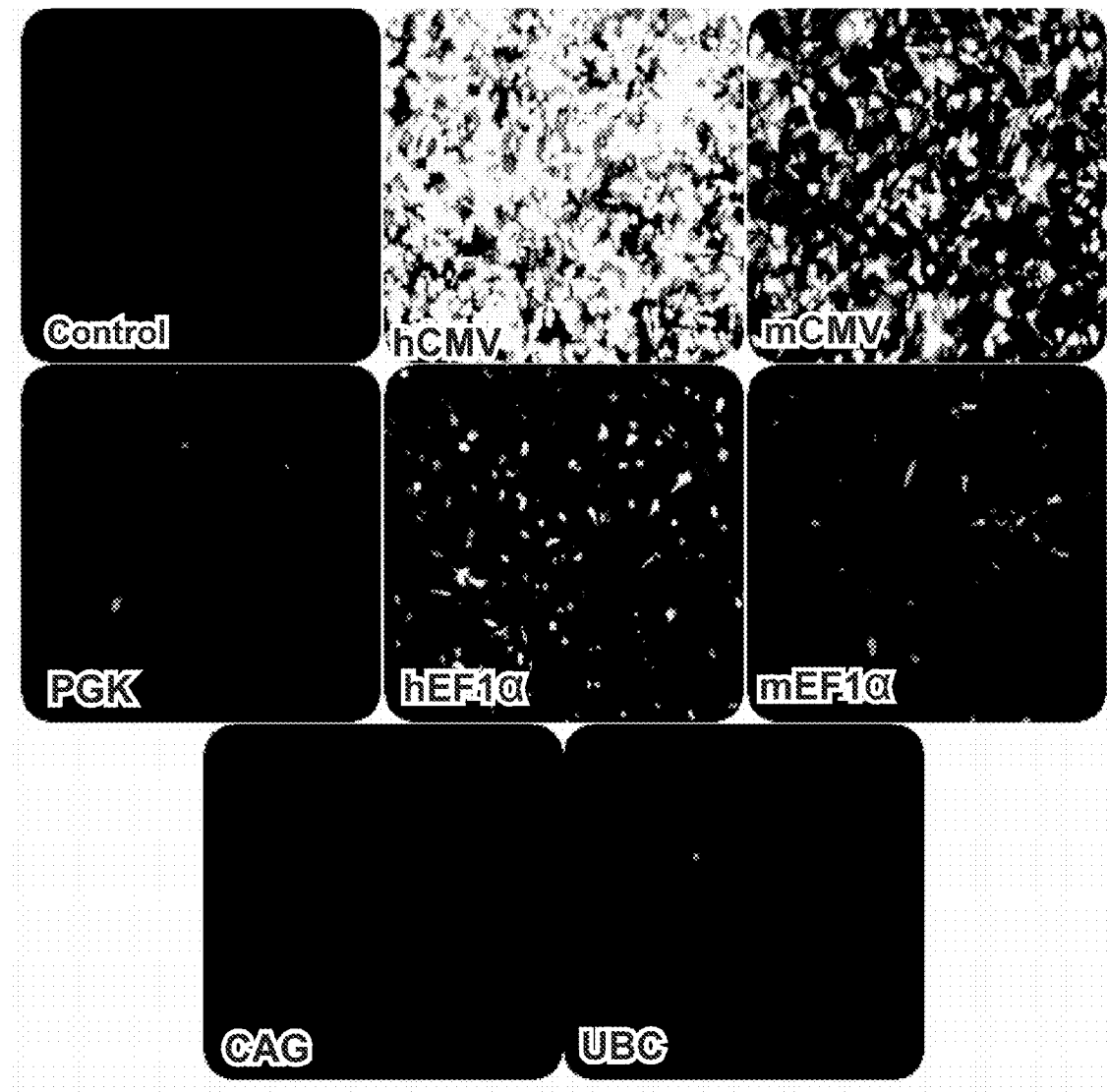
FIG. 1 is a representation of promoter activity as measured by GFP fluorescence from the results of example 1 in PC3 cells.

According to a first embodiment, the present invention provides a plate for selection of a promoter sequence. The plate comprises a first row of a first plurality of loci and a second row of a second plurality of loci. Each of at least two of the first plurality of loci within the first row comprises a first lentiviral vector and each of at least two of the second plurality of loci within the second row comprises a second lentiviral vector. In some embodiments, all loci within the first row comprise a first lentiviral vector, and all loci within the second row comprise a second lentiviral vector. Each row may, for example, have 2-12 or 3-9 or 4-6 loci. In some embodiments, each row has the same number of loci.

Preferably, each lentiviral vector comprises a promoter sequence, a reporter sequence, a miRNA scaffolding sequence, a mature strand insert sequence, and a star strand insert sequence. As persons of ordinary skill in the art will recognize, a mature strand insert sequence and a star strand insert sequence are examples of genetic content of interest. The sequences of the lentiviral vector may be part of a continuous linear or circular polynucleotide, and arranged in the aforementioned order or in any other order that a person of ordinary skill in the art would recognize as being advantageous for use in connection with the present invention.

A "promoter sequence" is a nucleotide sequence that is typically located upstream of another sequence and that provides a control point for transcription. In selecting a promoter sequence for use in connection with the present invention, in some embodiments, preferably the promoter sequence is suitable for microRNA-adapted designs. Thus, in some embodiments, one may wish to avoid using H1 and U6 promoters. By way of non-limiting examples, the promoter sequence may be selected from the group consisting of promoter sequences for hCMV, mCMV, hEF1α, mEF1α, CAG, hPGK, mPGK, and UBC or the group consisting of promoter sequences for hCMV, mCMV, hEF1α, mEF1α, CAG, mPGK, and UBC. Preferably, each vector will have only one promoter sequence. Examples of promoter sequences are SEQ ID NO: 1 (hCMV promoter); SEQ ID NO: 2 (mCMV promoter); SEQ ID NO: 3 (hEF1α promoter); SEQ ID NO: 4 (mEF1α promoter); SEQ ID NO: 5 (CAG promoter); SEQ ID NO: 6 (mPGK promoter); and SEQ ID NO: 7 (UBC promoter).

A "reporter sequence" is an oligonucleotide sequence that codes for proteins that facilitate assessment and optimization of transduction efficiency and promoter activity. By way of non-limiting examples, the reporter sequence may be selected from the group consisting of a sequence for tGFP, which codes for proteins that provide for green fluorescence, or tRFP, which codes for proteins that provides for red fluorescence. In some embodiments the reporter sequence is selected so as to enable a user to select a reporter that fluoresces in the red/orange end of the spectrum and to avoid conflict with an assay that may involve a signal that is in the yellow/green range.

A "miRNA scaffolding sequence" is an oligonucleotide that is derived from a microRNA. MicroRNAs are the endogenous substrates of the RNAi pathway, and microRNAs are transcribed as stem-loop structures that contain imperfect base-pairing in the stem. In a cell, microRNAs may be processed by multiple elements of the RNA pathway to generate duplexes that are approximately 18-30 base pairs in length and that are capable of associating with RISC to target genes for silencing. If the nucleotides that would ultimately form the microRNA (the 18-30-mer) are removed, what remains is deemed the scaffolding. As persons of ordinary skill in the art know, target sequences can be incorporated into these scaffoldings. By way of non-limiting examples, the miRNA scaffolding sequence may be derived from an endogenous pri-miRNA sequence, e.g., pri-miR-196a-2 or pri-miR-204. By using a miRNA scaffolding one can introduce shRNA and reduce or eliminate concerns about toxicity both in vitro and in vivo.

A "mature strand insert sequence" is a sequence that is incorporated or inserted into an miRNA scaffolding. The sequence may be 18-30 or 19-25 or 19-23 or 19-21 or 18-23 nucleotides long. In some embodiments, the mature strand insert sequence is at least 65%, at least 70%, at least 80%, at least 90%, at least 95% or 100% complementary to a target sequence. The mature strand insert sequence may be derived from an miRNA that is not the scaffolding or it may be derived from a target sequence that is not an miRNA or it may be random or pseudo-random or of an unknown derivation. For example, it may have less than 100%, less than 80%, less than 60%, less than 40% or less than 20% similarity to the miRNA sequence of the scaffolding, to any human miRNA sequence, to any mammalian miRNA sequence or to any miRNA sequence of any species. In some embodiments, the mature strand insert sequence is a non-targeting control ("NTC") sequence. A "non-targeting control" sequence is a sequence that does not target a specific mRNA or miRNA or other genetic sequence, i.e., is selected so as not to be complementary to a sequence that is known or expected to be expressed in a cell line into which the vector is introduced. A NTC sequence is preferable because it does not target or knockdown any gene. Thus, it does not induce phenotypic changes within a cell that may interfere or lead one to misinterpret an assessment of promoter activity. Thus, by using a NTC sequence, a researcher can test a promoter without running a gene-silencing experiment.

A "star strand insert sequence" is a sequence that is partially or completely complementary to a mature strand insert sequence. As with the mature strand insert sequence, it may be inserted within the miRNA scaffolding. Preferably it is inserted sufficiently downstream or upstream of the mature strand insert sequence to allow the scaffolding to form its desired stem and loop structure. Additionally, in some embodiments, it is the same length as the mature strand insert sequence.

In some embodiments, the mature strand insert sequence and the star strand insert sequence are each 18-30 or 19-25 or 19-23 or 19-21 or 18-23 nucleotides in length. Also, in some embodiments, the star strand insert sequence and the mature strand insert sequence are each located within the miRNA scaffolding sequence and the mature strand insert sequence is at least 60%, at least 70%, at least 80%, or at least 90% complementary to the star strand insert sequence, and neither the mature strand insert sequence nor the star strand insert sequence comprise a sequence derived from an endogenous miRNA that comprises the pri-miRNA scaffolding.

By way of further example, the star strand insert sequence may be 100% complementary to the mature strand insert sequence or it may be 100% complementary to the mature strand insert sequence, except that within a duplex formed between the star strand insert sequence and the mature strand insert sequence the duplex contains mismatches or wobble pairs at one or more of positions 1, 5, 12, 18, and/or if present at any or all of positions 19-23 of the mature strand insert sequence of the duplex.

As persons of ordinary skill in the art will recognize, the scaffolding need not necessarily be derived from a pri-miRNA sequence and in some embodiments, the lentiviral vector can omit the scaffolding, mature strand insert sequence and star strand insert sequence. In these embodiments, there may be a non-targeting control sequence or a sequence that targets a specific oligonucleotide. In some embodiments, the NTC shRNA in a vector may be expressed within the context of its flanking miRNA sequences, i.e., the scaffolding. The RNA transcript that contains the NTC shRNA may be designed to be identical to a transcript that contains a targeting shRNA sequence with respect to secondary structure, Drosha processing and Dicer processing. Thus, the processed shRNA hairpin will be present, but based on an algorithmic determination may be designed so that it does not bind to any known transcript or any known transcript of a species such as humans, and thus does not suppress gene expression. In some embodiments, a sequence corresponding to a mammalian drug selection marker such as a puromycin resistant marker (PuroR) is used. These types of markers facilitate selection and isolation of clonal populations when generating stable cell lines. Other markers that may be used include but are not limited to fluorescent proteins, drug selectable markers, and luciferase.

In some embodiments, it is preferable to include structural genes for broad tropism. By way of a non-limiting example, the lentiviruses may be designed to express virus envelope glycoprotein (VSVg), which is expressed on the surfaces the vesicular stomatitis virus. Pseudotyping lentiviral vector particles with VSVg confers broad tropism and allows end-users to work with a wide range of cell types. Additional glycoprotein pseudotypes further expanding the tropism of lentiviral vector particles include but are not limited to mouse retroviral envelopes (ecotropic and amphotropic), rabies virus G protein, and Ebola virus glycoprotein.

Within the plates of various embodiments of the present invention, each of the plurality of loci within the second row comprises a second lentiviral vector, wherein the second lentiviral vector is the same as the first lentiviral vector except that it comprises a different promoter sequence. For example, the promoter sequence may be a promoter selected from the group consisting of promoter sequences for hCMV, mCMV, hEF1α, mEF1α, CAG, hPGK, mPGK, and UBC or from the group consisting of promoter sequences for hCMV, mCMV, hEF1α, mEF1α, CAG, mPGK, and UBC.

In some embodiments, the plate further comprises a third row of a plurality of loci, wherein at least two or each of the plurality of loci within the third row comprises a third lentiviral vector that is the same as the first lentiviral vector, except that it contains a different promoter sequence. For example, the promoter sequence may be selected from the group consisting of promoter sequences for hCMV, mCMV, hEF1α, mEF1α, CAG, hPGK, mPGK, and UBC and be different from the promoter sequences of the first lentiviral vector and of the second lentiviral vector. Optionally, hPGK is omitted from the group from which the promoter sequence for the third lentiviral vector is selected.

In some embodiments, the plate further comprises a fourth row of a plurality of loci, wherein at least two or each of the plurality of loci within the fourth row comprises a fourth lentiviral vector that is the same as the first lentiviral vector, except that it contains a different promoter sequence. For example, the promoter sequence may be selected from the group consisting of sequences for hCMV, mCMV, hEF1α, mEF1α, CAG, hPGK, mPGK, and UBC and be different from the promoter sequences of the first lentiviral vector, of the second lentiviral vector and of the third lentiviral vector. Optionally, hPGK is omitted from the group from which the promoter sequence for the fourth lentiviral vector is selected.

In some embodiments, the plate further comprises a fifth row of a plurality of loci, wherein at least two or each of the plurality of loci within the fifth row comprises a fifth lentiviral vector that is the same as the first lentiviral vector, except that it contains a different promoter sequence. For example, the promoter sequence may be selected from the group consisting of promoter sequences for hCMV, mCMV, hEF1α, mEF1α, CAG, hPGK, mPGK, and UBC and be different from the promoter sequences of the first lentiviral vector, of the second lentiviral vector, of the third lentiviral vector and of the fourth lentiviral vector. Optionally, hPGK is omitted from the group from which the promoter sequence for the fifth lentiviral vector is selected.

In some embodiments, the plate further comprises a sixth row of a plurality of loci, wherein at least two or each of the plurality of loci within the sixth row comprises a sixth lentiviral vector that is the same as the first lentiviral vector, except that it contains a different promoter sequence. For example, the promoter sequence may be selected from the group consisting of promoter sequences for hCMV, mCMV, hEF1α, mEF1α, CAG, mPGK, and UBC and be different from the promoter sequences of the first lentiviral vector, of the second lentiviral vector, of the third lentiviral vector, of the fourth lentiviral vector and of the fifth lentiviral vector. Optionally, hPGK is omitted from the group from which the promoter sequence for the sixth lentiviral vector is selected.

The plates may also contain a control row. The loci within a control row may in some embodiments have an absence of lentiviral vectors.

Figure 7:
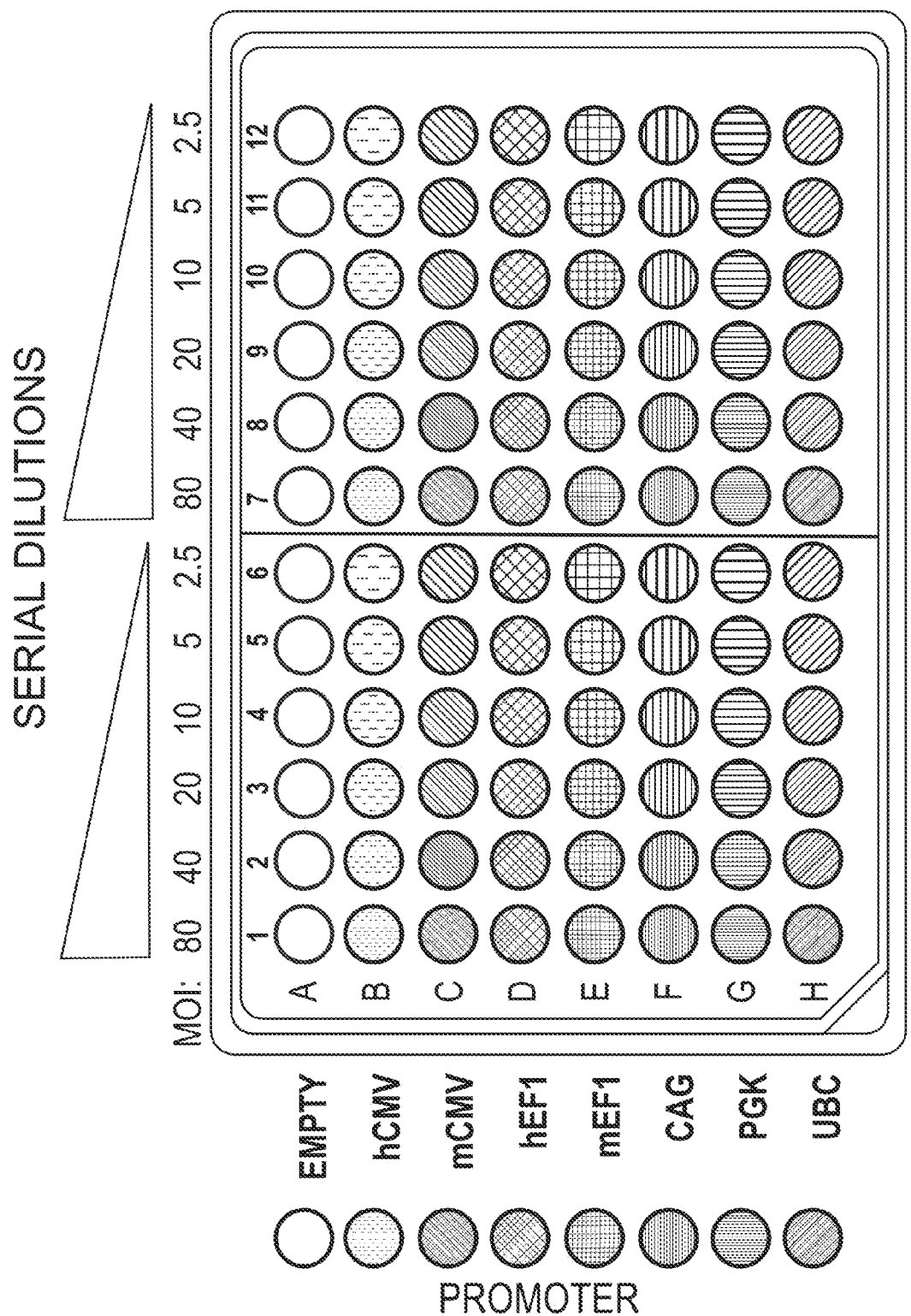
FIG. 7 is a representation of serial dilutions of test vectors in a plate according to an embodiment of the present invention.

Each plate may contain a consistent number of loci in each column, regardless of whether loci are used in an experiment and all or fewer than all may contain lentiviral vectors. For example, a plate may contain 12-96 or 24-96 or 36-96 loci or exactly 24, 36, 72, or 96 loci, which may be wells, and may be organized in, for example, 2-12 rows. Across a row, the amount of lentivirus in consecutive loci may be determined by serial dilutions. FIG. 7 illustrates a plate according to an embodiment of the present invention in which serial dilutions are performed. Dilutions may for example be 2 fold, 3 fold, 4 fold, 5 fold, 6 fold, etc. between consecutive loci. Preferably, viral particles with a stated dilution or in the same plate column have equivalent titer, and transductions are performed under the same conditions. The rows B through H in the figure represent experiments in which different promoters are used (hCMV, mCMV, hEF1, mEF1, CAG, PGK and UBC); row A is empty. The columns represent two sets of serial dilutions that correspond to each promoter. The Multiplicity of Infection ("MOI") for each locus may for example be, 80, 40, 20, 10, 5, and 2.5. Through the use of these plates, a researcher can test biological duplicates and MOIs ranging from very low (2.5 Transducing Units (TUs)/mL) to very high (80 TU/mL) using concentrated high-titer lentiviral particles in a single experiment. For accurate assessment of promoter activity, lentiviral particles may, for example, be normalized with regard to titer as determined by p24 ELISA. As persons of ordinary skill in the art will recognize, a multiplicity of infection refers to the ratio of infectious agents to infection targets, e.g., cells.

According to another embodiment, the present invention provides a method for suppressing gene expression. In this method, first one transduces different wells of a cell line of interest with lentiviral vectors located at at least two different loci of a plate such as one of the plates described in this disclosure.

Next, one measures intensities of a signals generated by activity in the cells, thereby establishing a plurality of measured intensities. Notably in some embodiments, the lentiviral vectors contain non-targeting shRNA control sequences as their mature sequences. After the intensities are measured, one selects a promoter sequence for insertion into a suppression vector, thereby obtaining a selected promoter sequence, wherein the selected promoter sequence has the highest measured intensity at the lowest multiplicity of infection. The intensity may be greater than a predetermined level or noticeable to the human eye or machine that is calibrated to analyze intensities.

After selecting a promoter, one obtains a suppression vector. The suppression may comprise the selected promoter sequence; optionally a reporter sequence; an miRNA scaffolding sequence; a mature strand insert sequence; and a star strand insert sequence. The miRNA scaffolding sequence may for example be derived from an endogenous pri-miRNA sequence. The mature strand insert sequence and the star strand insert sequence may be defined as described above. In some embodiments, the suppression vector that is obtained omits a reporter sequence. Further, it may have an absence of a non-targeting control sequence and instead have a sequence that is selected based on its likelihood to suppress a target gene. Additionally, whereas the initial steps may be conducted in vitro, the suppression vector may subsequently be used either in vitro or in vivo. When used in vivo, the suppression vector may be used as part of a medicament and administered by methods now known or that come to be known and that a person of ordinary skill in the art would appreciate as being useful in connection with the present invention.

The method may further comprise applying an algorithm to a plurality of candidate mature strand insert sequences or candidate star strand insert sequences for the suppression vector. In various embodiments, the algorithm selects a target sequence on the basis of one or more variables, e.g., position dependent nucleotide preferences, secondary structures, thermodynamic stability profiles, and complementarity or homology to a target sequence. Additionally, the algorithm may contain seed-based filters that help to select sequences with either no off-target effects or satisfactorily low off-target effects.

The algorithm may for example, comprises at least one, at least two, at least three, at least five, at least ten, at least twenty, or at least thirty variables, wherein each of which has a value that is dependent upon the presence or absence of a base at at least one position of either a candidate mature strand insert sequence or a candidate star strand insert sequence. Additionally, the variables may be weighted different amounts and either positive or negative, and there may be additional variables such as the overall GC content or the GC content at specific positions and internal thermal stability. The output of the algorithm assigns a value to each of the candidate mature strand insert sequences or candidate star strand insert sequences and the value indicates a relative ranking of the candidate mature strand insert sequences or candidate star strand insert sequences. Examples of algorithms include but are not limited to those disclosed in U.S. Patent Publication Number 2005-0255487, published on Nov. 17, 2005 and in U.S. Patent Publication Number 2007-0031844, published on Feb. 8, 2007. The entire disclosure of each of these publications is incorporated by reference. A person of ordinary skill in the art may then select the mature strand (or star strand) insert sequence with the highest value or one of the top two, three, four, five or ten highest values for a target.

Figure 12:
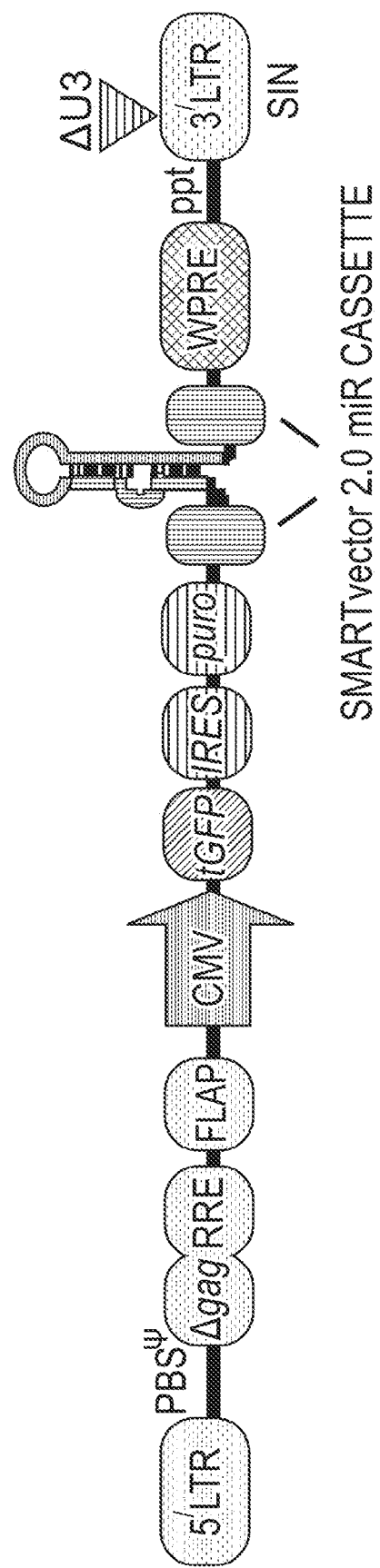
FIG. 12 is a representation of an example of configuration options for vectors of the present invention.

According to another embodiment, the present invention is directed to a lentiviral vector. The lentiviral vector may be any of the lentiviral vectors described in this disclosure regardless of whether used in connection with plates, methods or kits described herein. FIG. 12 is a representation of an example of configuration options of the vectors within the scope of the present invention. By way of a non-limiting example, the viral sequences contained in a vector genome may include:

1. A 5' long terminal repeat (LTR);
2. A primer binding site (PBS) complementary to tRNA$^{Lys3}$ for initiation of reverse transcription and minus-strand DNA synthesis;
3. A sequence encompassing the HIV-1 psi (ψ) packaging signal including a 5' terminal fragment of the gag sequence;
4. A env fragment that includes the Rev response element (RRE); the RRE is the sequence in viral RNA transcripts where HIV 1 Rev protein binds to facilitate export of these RNA transcripts out of the nucleus;
5. A 156 base pol fragment (FLAP) from coordinates 4327 to 4483 of HIV-1 SG3 molecular clone (see Ghosh, et. al. *Virology*, 194(2), 858-864, 1993, the entire disclosure of which is incorporated by reference) containing a central polypurine tract (cPPT) and central termination site (CTS), which is required for efficient translocation of the pre-integration complex across the nuclear envelope;
6. An internal promoter such as CMV controlling expression of the miR-adapted shRNA, fluorescent reporter, and puro-resistance gene;
7. shRNA sequence flanked by a miR scaffold;
8. TurboGFP or TurboRFP (Evrogen, Moscow, Russia) reporter genes;
9. The polypurine track (ppt), which facilitates initiation of plus-strand DNA synthesis; and
10. A 3' LTR that lacks the enhancer elements located in the U3 region needed for native transcriptional activity from the viral LTR. The deletion within the 3'-LTR results in a vector that is self-inactivating (SIN).

The lentiviral vectors may be administered in vivo or in vitro.

The various lentiviral vectors may be administered to cells from organisms such as mammals, including but not limited to humans and other primates such as chimpanzees, rats, mice, cats, dogs, sheep, horses, cows, etc., as well as to non-mammalian organisms such as, birds, reptiles and amphibians. They also may be administered directly to those organisms themselves or to cells of specific cell lines. Examples of cells from cell lines include but are not limited to the group consisting of HeLa, Ovcar-8, Jurkat, A549, IM-9, CD4, NiH3T3, J774, ES-D3, ES-E14TG2a, RAW 264 and C2C12. In some embodiments, the lentiviral vector that is administered contains a promoter that is not human CMV. In some embodiments a promoter is considered not to be a human CMV promoter if it is not identical to an endogenous human CMV promoter, or is at least 2% or at least 5% or at least 10% or at least 20% or at least 30% or at least 40% or at least 50% different from an endogenous human CMV promoter sequence, the sequence of which is disclosed in U.S. Pat. Nos. 5,168,062 and 5,385,839, the entire disclosures of which are incorporated by reference. Notably, by using the plates described above, one can test different combinations of promoters, reporters, scaffoldings and mature strand/star strand insert sequences in each of these cells in order to determine when a lentiviral construct would be most effective. In some embodiments, in order to compare the effects of an element, between any two rows of a plate only one element of a construct is varied while all other elements are held constant.

According to another embodiment, the present invention provides a kit for suppressing gene expression comprising a plurality of lentiviral vectors described in this disclosure. The plurality of lentiviral vectors may comprise at least two, at least three, at least four, at least five or at least six lentiviral vectors that have different promoter sequences. In some embodiments, except for differences in promoter sequences, the lentiviral vectors are otherwise identical. In some embodiments on the same plate, one can vary other variables as well, such as mature strand/star strand sequences or reporters to test for the effects of each of these elements alone, as well as to look for synergies.

Kits may also include cell lines or be used with cell lines. Cell lines that prefer human CMV promoters include but are not limited to the human cell lines HEK293T, MCF7, MDA-MB-231, HCT116, PC3 and IMR32; rat cell line H9c2; and hamster cell line CHO-K1. Cell lines that prefer other promoters include the human cell lines HeLa, Ovcar-8, Jurkat—T cells in suspension, A549, IM-9—B cells in suspension, and CD4+ T cells—primary cells; and the mouse cell lines NIH3T3, J774—macrophage, ES-D3—stem cells, ES-E14TG2a—stem cells, RAW 264.7—macrophage and C2C12 cells. The kits may be used to discover highly active promoters in particular cell lines such as the mEF1α promoter in the human-T-cell line Jurkat.

In one embodiment, the kit comprises one or more if not all of: a 96-well plate of the present invention with transduction ready lentiviral vector particles arranged in the wells and produced from vectors containing various promoters. Examples of other components may be one or more of polybrene, one or more multichannel pipettors, cell(s) of choice (e.g., primary cells, hematopoietic cells), DMEM (Thermo Scientific, HyClone), a culture medium that is supplemented with or without antibiotics (e.g., Pen-Strep), base media that corresponds to the preferred culture medium containing no serum or other supplements such as antibiotics, and transduction media corresponding to a 1:1 Base Media to DMEM, preferably containing no serum or other supplements.

According to another embodiment, a researcher may purchase or otherwise acquire a kit of the present invention. In some embodiments, the kit may contain vectors with one to seven (i.e., one, two, three, four, five, six or seven) different promoters and may contain a 96-well plate. When in use, the researcher may leave one row empty as a control and conduct experiments in serial dilutions. In a 96 well plate, there may be twelve columns, which will permit the researcher to run two sets of six wells for each promoter with various levels of transducing units (T.U.) within each set. Conditions for transduction known to persons of ordinary skill in the art may be used. The researcher may add particles of the cells of interest, which preferably were optimized for cell density, polybrene, and serum. The plate may be allowed to sit for 48-96 hours, at which time the researcher may analyze the fluorescence, which may for example, be GFP intensity. The researcher may then choose the promoter with the highest fluorescence intensity at the lowest MOI or at the lowest MOI for which intensity is detected. The researcher may then synthesize either enzymatically or chemically a suppression vector of choice or order one from a commercial source that contains the genetic content of interest. For example, the lentivirus may be ordered from Thermo Fisher Scientific in the form of a SMARTvector 2.0 lentiviral shRNA vector that is constructed with the promoter of choice. Lentiviral vector particles may then be produced. Thus, the lentiviral particle may be designed with the desired promoter, control, scaffolding and gene(s) of interest.

Below is a sample protocol of how to use various embodiments of the present invention.

Transduction

Day 1: Prepare a culture plate by seeding cells of choice into a 96-well tissue culture-treated plate. Seed the appropriate number of cells that will result the following day in a confluency of 40-60% at the time of transduction. Seed cells in a total of 100 µL of a culture media. Place the culture plate in an incubator overnight under the appropriate conditions. Non-adherent or suspension cells should be counted and plated at the time of transduction, and not incubated overnight.

Day 2: Perform the viral transductions using the procedures described below.

Step 1. Prepare the promoter selection plate for transduction:

2.1. Thaw viral particles on ice. After the viral particles have thawed, spray plate with 70% ethanol and carefully wipe excess from plate with paper towel.

2.2. Quick-spin viral particles to the bottom of the well by centrifuging (rcf=300) for 20-40 seconds in a table top centrifuge. Remove plate from centrifuge. Clean both the inside of the centrifuge and the promoter selection plate using 70% ethanol. Carefully wipe plate with paper towel.

2.3. Within a Class II/Type A2 biological safety cabinet, carefully remove foil seal from the promoter selection plate being careful not to shake viral particles out of the wells. Immerse the foil seal in a liquid waste reservoir. Remove the foil seal from the beaker and dispose of it into the biohazardous waste bag.

2.4. To each well of the Promoter Selection Plate, pipette 30 µl of Base Media. This essentially results in the same formulation as the Transduction Media (1:1 mixture of DMEM:Base Media) that is described above. At this time add Polybrene and serum (if necessary), at the pre-determined concentrations, to the Base Media prior to adding to the viral particles. This is done by adding Polybrene (and serum) to the Base Media at a 2× concentration, as transferring 30 µl of Base Media+Polybrene into 30 µl of viral particles will result in a 1× Polybrene concentration. Place a new Foil Seal over plate and quick-spin plate by centrifuging (rcf=300) for 20-40 seconds in a table top centrifuge. An eight-channel multi-channel pipettor is recommended for all transfers to and from the Promoter Selection Plate. Use new tips for each transfer and deactivate any lentiviral particles in pipette tips by aspirating and dispensing bleach or Lysol® into and out of the tips prior to disposal. The 60 µl total volume per well (30 µl viral particles in DMEM and 30 µl of Transduction Media) is referred to as the Transduction-Ready Media.

2.5. Incubate plate at room temperature for 10-20 minutes. If Polybrene is not added, skip this step and proceed immediately to Step 2.6.

2.6. Next, quick-spin plate by centrifuging (rcf=300) for 20-40 seconds in a table top centrifuge.

2.7. Take the culture plate from the incubator and place it in the biological safety cabinet. Using a multichannel pipettor, carefully aspirate the preferred culture medium from each well of the culture plate being careful not to dislodge the cells from the bottom of the well. Dispense the preferred culture medium into a liquid waste reservoir.

2.8. Carefully remove the foil seal. Transduce cells by transferring 50 µL of the Transduction-Ready Mix from each well of the promoter selection plate to the corresponding wells of the culture plate. An eight-channel multichannel pipettor may be used to transfer Transduction-Ready Mix one plate column at a time. Tips should be changed following each transfer and deactivated in the liquid waste reservoir before disposal. After all dilutions (columns) of the Transduction-Ready Mix are transferred to the corresponding wells, place culture plate in incubator and culture under the appropriate conditions.

2.9. Allow transduction to proceed for 6 hours or overnight if tolerated by the cells. After the transduction period, add 100 µL, of preferred culture medium directly to each well. Adjust serum concentration accordingly.

2.10. Culture the transduced cells under the appropriate conditions for 48 to 96 hours.

Non-adherent cells should be counted and plated just prior to transduction. After determining the cell concentration, transfer enough suspension cells according to the desired cell density into a sterile centrifuge tube. Pellet cells by centrifuging (rcf=300) for 4 minutes in a table top centrifuge. Following centrifugation, carefully aspirate the supernatant. Gently re-suspend the cell pellet in 3750 µL of base media, then plate 25 µL cells/base media suspension into each well of the 96-well culture plate. For example, if $1.5 \times 10^6$ cells were polluted and re-suspended in 3750 µL of base media, then 25 µL would correspond to 10,000 cells per well. Prepare the promoter selection plate for transduction using the procedures described above. Transduce cells by transferring 50 µL of the Transduction-Ready Mix from each well of the promoter selection plate to the corresponding wells of the culture plate. Allow transduction to proceed for six hours. As suspension cells settle over time to the bottom of the well, it is recommended that one gently rock or tap the plate every 30-60 minutes to mix the cells with the viral particles. This should be done in a Class II/Type A2 biological safety cabinet. For more thorough mixing, one may gently pipette up-and-down 5-10 times using a multichannel pipettor. One should change pipette tips from one column to the next and deactivate the tips in the liquid waste beaker before dispensing. Following the transduction period, add 75 µL of the preferred culture medium directly to each well. Supplement the preferred culture medium with additional serum and reagents as described above. Allow cells to culture under appropriate conditions for 48-96 hours.

Next one may analyze promoter activity by GFP fluorescence. First, one may visually inspect cultures daily using fluorescence microscopy. Various methods can be utilized to analyze and to quantify GFP fluorescence. Two methods, fluorescence microscopy and flow cytometry, are described below.

Fluorescence Microscopy

Figure 3:
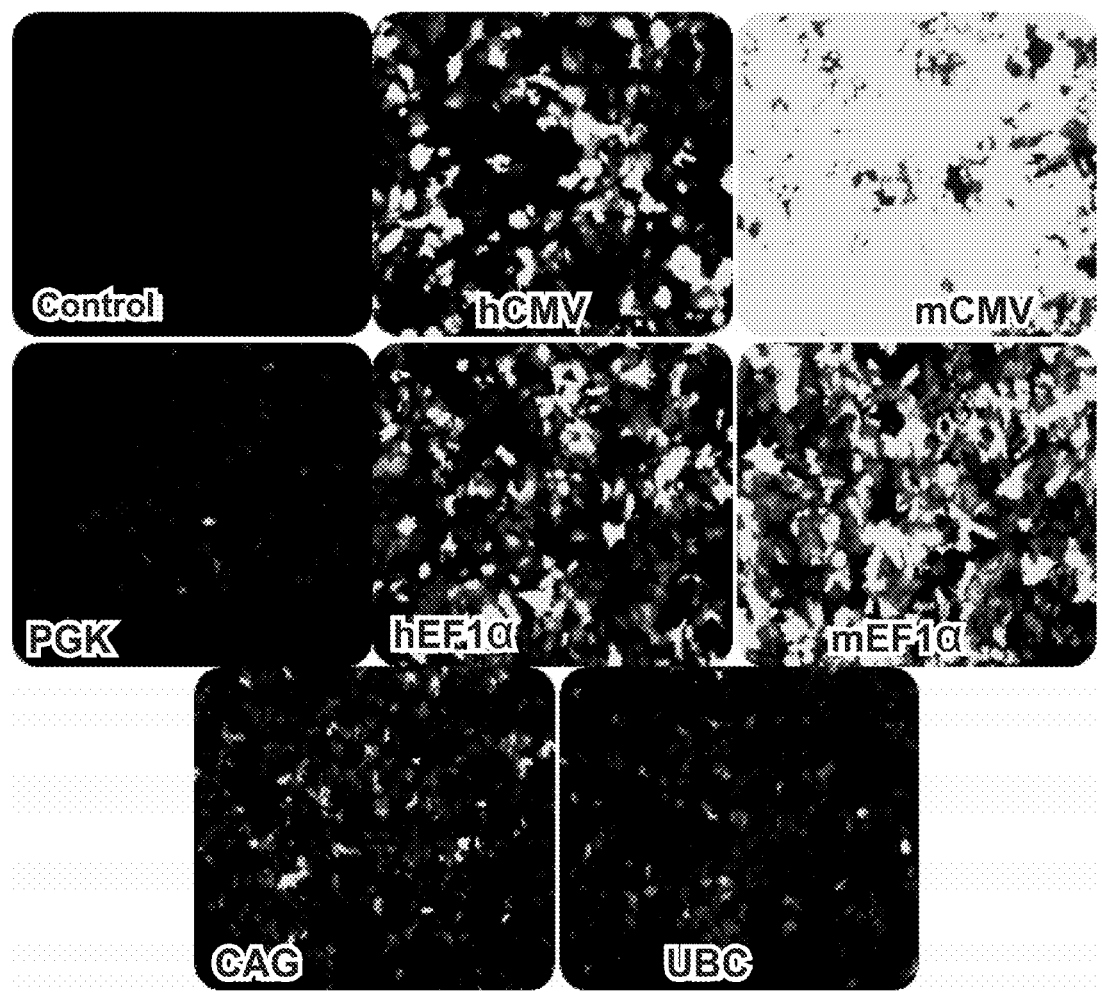
FIG. 3 is a representation of promoter activity as measured by GFP fluorescence from the results of example 2 in A549 cells.

Visually inspect cultures daily using fluorescence microscopy. Fluorescence microscopy is described below, but other methods such as flow cytometry could be utilized. Promoter activity can be qualitatively assessed using fluorescence microscopy. Comparing promoter activity between the seven promoters is done by visually scoring TurboGFP fluorescence intensity. FIG. 3 depicts the fluorescent images of human A549 cells transduced with viral particles from a SMARTchoice™ Promoter Selection Plate.

As shown in FIG. 3, the mouse CMV promoter consistently ranked highest in fluorescence intensity and therefore would be the optimal promoter choice for delivery and expression in the cells of interest. Generally, there will be a clear choice as to which promoter is the most active in the cell of interest. Furthermore, the highest ranked promoter for a particular cell line should be consistent across all six concentrations. In the above example, the mouse CMV promoter ranked highest at all concentrations tested.

Next one may test for long-term expression. The expression of many cellular genes is modulated by epigenetic modifications such as DNA methylation and histone acetylation. Often promoter elements are targets of these epigenetic changes, including promoters present on mammalian expression vectors, resulting in promoter silencing. As with promoter activation, silencing is cell type dependent, with promoters becoming shut down in some cells while staying constitutively active in others.

The promoter selection plate can also be used to test whether the promoter can sustain expression in a particular cell line. Because lentiviral vectors integrate stably into the host cell chromosome, cells transduced with the viral particles of the present invention can be passaged in definitely in culture. Monitoring and quantifying GFP fluorescence over time provides a good measure of promoter stability in the cell of interest. Decreased fluorescent intensity over time may be an indication that promoter silencing is occurring. The time it takes for the promoter to begin silencing as well as the degree of silencing can differ from cell to cell. One may use the following protocol to determine if the promoters become silenced over time in the cell of interest.

Next one may engage by selection, e.g., puromycin selection, for the promoter silencing assay. Puromycin selection can be used to remove all untransduced cells in the culture. Removal of the untransduced cells will diminish the possibility of these cells from becoming the predominant cell in the culture, thereby making it difficult to assess promoter silencing. Prior to embarking on the promoter silencing assay, the minimal concentration of puromycin needed to eliminate all untransduced cells within 4-6 days may be determined. The following protocol describes how to determine the optimal puromycin concentration.

Day 1: Using the same cell type and relative cell densities to be used in subsequent transduction procedures, plate cells and culture overnight.

Day 2: Replace complete growth medium with growth medium supplemented with a range of puromycin concentrations (0.1-10 µg/mL).

Day 4: Refresh medium and assess viability.

1. Replace medium with fresh medium supplemented with the appropriate concentration of puromycin every 2 days.

2. Examine cells daily and identify the minimal concentration of puromycin that efficiently kills all untransduced cells between 4-6 days following addition of puromycin.

Follow the protocol as described above for transducing cells using the promoter selection plate, one may then run an assay for promoter silencing.

Two days post-transduction, observe and image (if possible) cells using fluorescent microscopy. If imaging cells, record all imaging parameters, including exposure time.

Begin passaging cells in the 96-well culture plate using the preferred medium containing the predetermined concentration of puromycin sufficient to select for successfully transduced cells. Cells should be passaged every 2-3 days.

Take fluorescent images of cells just before each passage using the same exposure time.

Maintain cells in culture for 2 weeks.

Analyze fluorescent images for evidence of promoter silencing.

Next one may use a customized vector

The intent of the promoter selection plate is to determine by empirical observation the promoter that is optimal for expressing a shRNA in the cell of interest. The vector is amenable to modularization of vector elements, as the shRNA designs reside in silico until ordered. Vectors such as Dharmacon's SMARTvector 2.0 shRNA can be made available with any one of a plurality of promoters. SMARTvector 2.0 also can be constructed with for example either turbo GFP or turbo RFP (Evrogen) as the fluorescent marker.

Viral Packaging and Titer.

During the preparation of lentiviral particles, the transfer plasmid (containing the shRNA gene-targeting construct) and the helper plasmids are co-transfected into cells. The viral vector genomes are produced, encapsulated and released as virion particles from the cells into the surrounding medium. Transduction of cells with this viral supernatant (medium containing the viral particles) can be performed at low or high multiplicities of infection (MOI). Lower MOIs may be used for more easily transduced cells or when establishing stable cell lines. High MOIs may be needed for difficult-to-transduce cell lines or in vivo applications; however, it is important to note that addition of large volumes of low titer viral supernatant can often be toxic. This is due in part because the viral supernatant also contains cellular debris (metabolites, nucleases and proteases) derived from the packaging and production process that will affect the viability of transduced cells.

In order to increase stability and storage, strategies to employ may be: the vectors are shipped on dry ice as 25 µL aliquots and must be stored at −80° C. Under these conditions, particles are stable for at least 6-12 months. Repeated freeze-thaw cycles should be avoided as this can negatively affect viral titer. When setting up a gene knockdown experiment using gene silencing reagents, viral particles should be thawed on ice, aliquoted into smaller volumes (if necessary) and immediately returned to −80° C.

Reference has been made in detail to certain embodiments of the invention, examples of which are illustrated in the accompanying figures. While the invention is described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

EXAMPLES

Example 1

Cellular Dependent Promoter Activity

Non-targeting control vectors that had different promoters were transduced into two cells lines. Seven different promoters were tested and a control was run that did not contain any vector.

The experimental conditions were:
Cell density: 50,000 per well in a 24-well plate.
MOI 15.
Time point of observation: 72 hours.
Assay: visual examination of GFP.
Gene targeted: none.
Fluorescent proteins being measured: GFP.
Control: empty.
Promoters used: hCMV, mCMV, mPGK, hEF1α, mEF1α, CAG, and UBC.
Cell lines in which experiments were run: PC3: human prostate cancer; and OVCAR8: human ovarian cancer.

Figure 2:
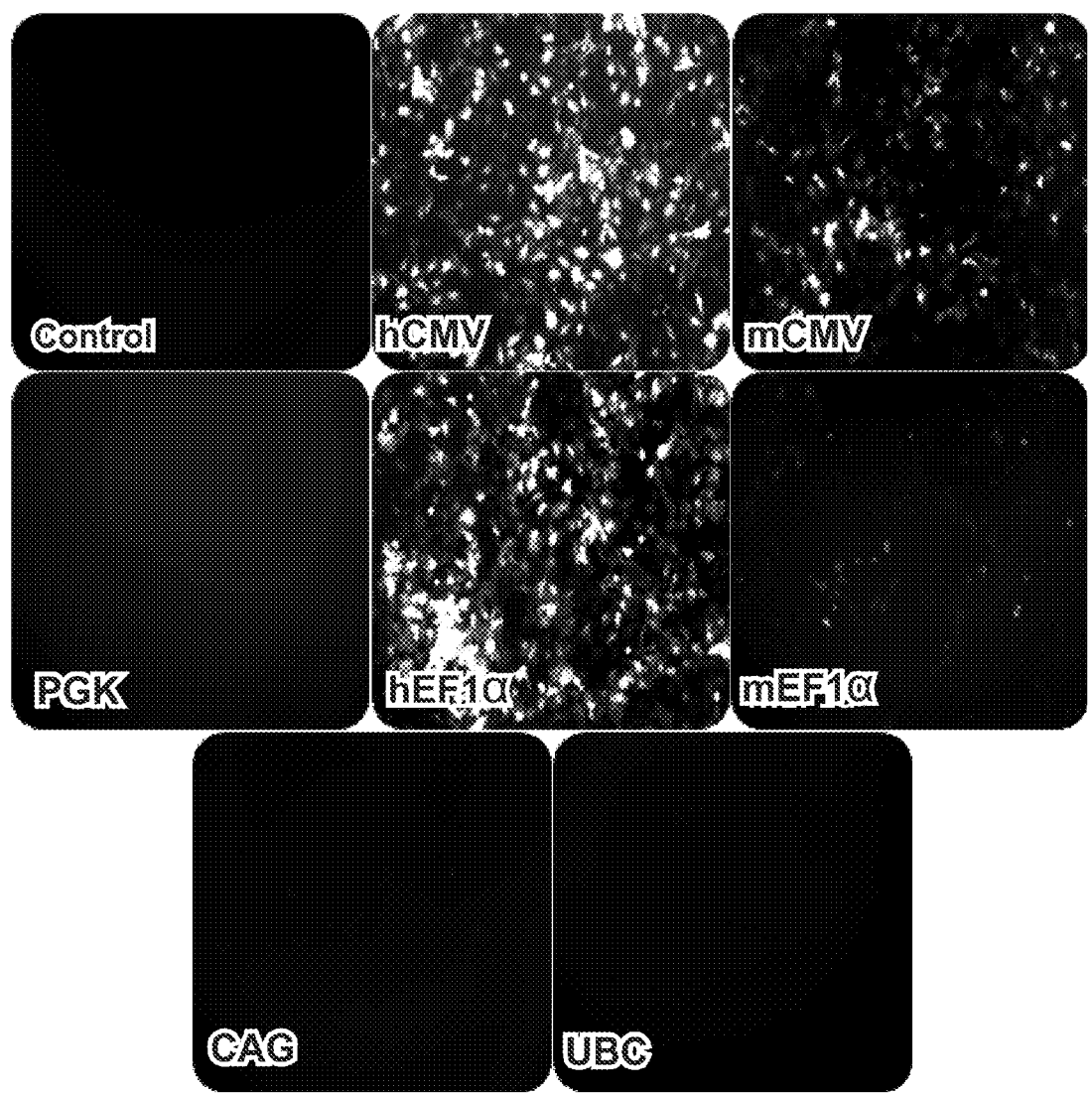
FIG. 2 is a representation of promoter activity as measured by GFP fluorescence from the results of example 1 in OVCAR8 cells.

FIG. 1 shows the results in PC3 cells and FIG. 2 shows the results in OVCAR8 cells. As these results demonstrate, different promoters can have different activity depending on the cell type. Whereas for the PC3 cells the human CMV promoter yielded the greatest fluorescence and the mouse CMV yielded the second greatest fluorescence, in the OVCAR8 cells, the two promoters that yielded the greatest fluorescence were hCMV and hEF1α. Thus, promoter activity can vary across cell lines.

Example 2

Cross-Species Promoter Activity

Non-targeting control vectors that had different promoters were again transduced into two cells lines from two different species. Seven different promoters were tested and a control was run that did not contain any vector.

Figure 4:
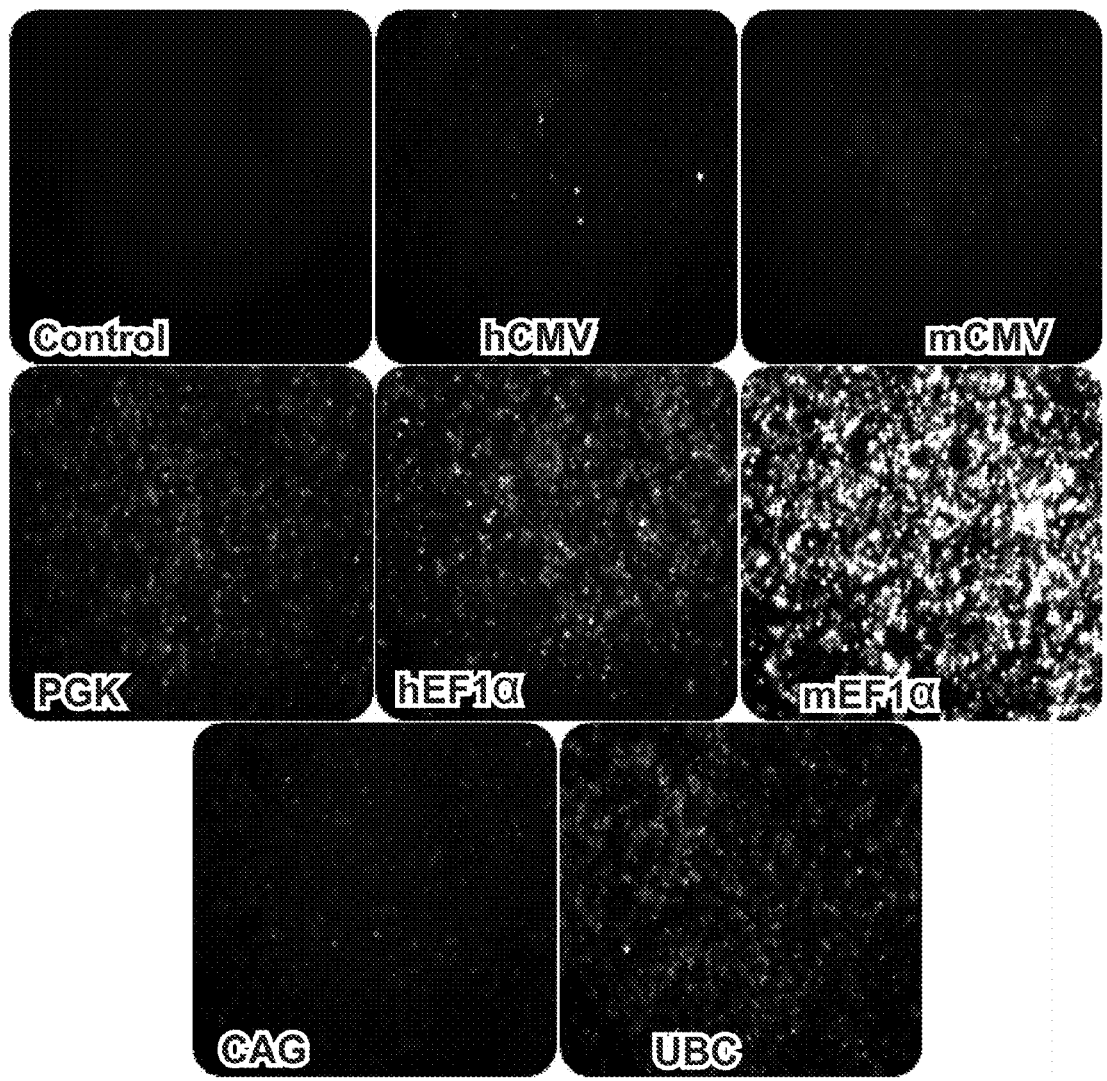
FIG. 4 is a representation of promoter activity as measured by GFP fluorescence from the results of example 2 in Jurkat cells.

The experimental conditions were:
Cell density: 50,000 per well in a 24-well plate.
MOI 15.
Time point of observation: 72 hours.
Assay: visual examination of GFP.
Gene targeted: none.
Fluorescent proteins being measured: GFP.
Control: empty.
Promoters used: hCMV, mCMV, mPGK, hEF1α, mEF1α, CAG, and UBC.
Cell lines in which experiments were run: A549: human lung carcinoma; and Jurkat: human T lymphocyte. FIG. 3 shows the results in A549 cells and FIG. 4 shows the results in Jurkat cells. As these results demonstrate, the most active promoter is not always predicted based on the species a particular cell line or promoter is derived. In the above examples, the human-derived promoters (hCMV and hEF1α) are not the most active in the two human cell lines. Instead, the mouse-derived promoters (mCMV and mEF1α) are the most active.

Example 3

Promoter Activity Reflects Gene Knockdown

Non-targeting control vectors that had different promoters were transduced into cells from a cell line. Seven different promoters were tested and a control was run that did not contain any vector.

The experimental conditions were:
Cell density: 50,000 per well in a 24-well plate.
MOI 15.
Time point of observation: 72 hours.
Assay: visual examination of GFP.
Gene targeted: none.
Fluorescent proteins being measured: GFP.
Control: empty.
Promoters used: hCMV, mCMV, PGK, hEF1α, mEF1α, CAG, and UBC.

Figure 5:
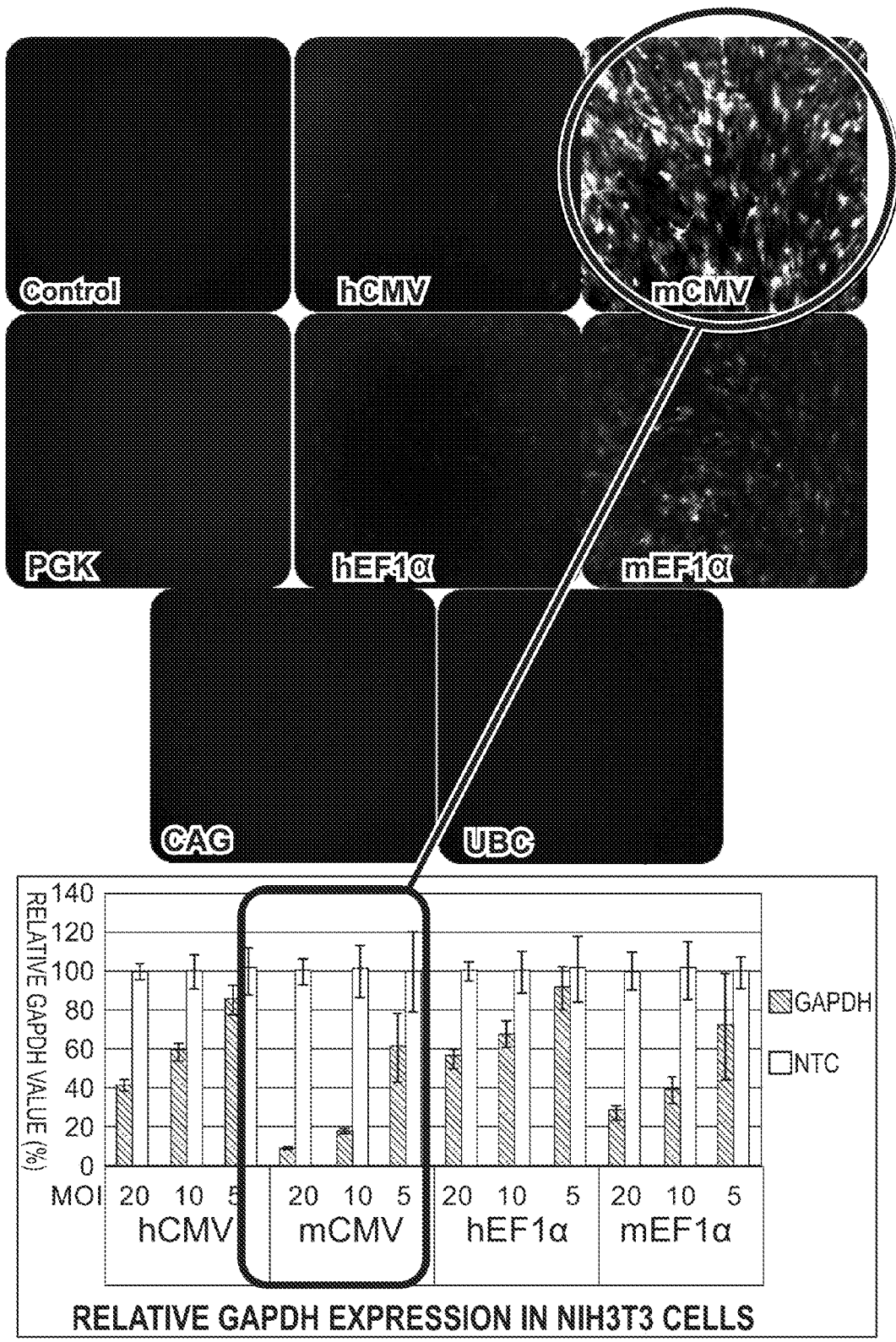
FIG. 5 is a representation of promoter activity as measured by GFP fluorescence from the results of example 3 in NIH3T3 cells and a measure of relative GAPDH expression following expression from four different promoters of an shRNA targeting GAPDH.

Cell line in which experiments were run: NIH3T3: mouse embryo fibroblast. FIG. 5 (top) shows the greatest fluorescence with the mouse CMV promoter. FIG. 5 (bottom) shows a bar graph that contains the result of an experiment conducted under the following conditions:
Cell density: 50,000 per well in a 96-well plate.
MOI 20, 10 or 5, as indicated.
Time point of observation: 72 hours.
Assay: solaris QPCR.
Gene targeted: GAPDH.
Normalization method: based on 18S expression.
QPCR conditions: based on solaris protocol: 95 C, 10 min, followed by 40 cycles of 95 C, 15 seconds and 60 C, 60 seconds.

The qualitative assessment of the most active promoter as evidenced by GFP expression correlates with the quantitative measurement of housekeeping gene knockdown.

Example 4

Promoter Activity Reflects Gene Knockdown

Empty vectors that had no shRNA but that had different promoters were transduced into cells from a cell line. Seven different promoters were tested and a control was run that did not contain any vector.

The experimental conditions were:
Cell density: 50,000 per well in a 24-well plate.
MOI 15.
Time point of observation: 72 hours.
Assay: visual examination of GFP.
Gene targeted: none.
Fluorescent proteins being measured: GFP.
Control: empty.
Promoters used: human CMV, mouse CMV, PGK, hEF1α, mEF1α, CAG, and UBC.
Cell line in which experiments were run: A549: human lung carcinoma (mouse CMV).

Figure 6:
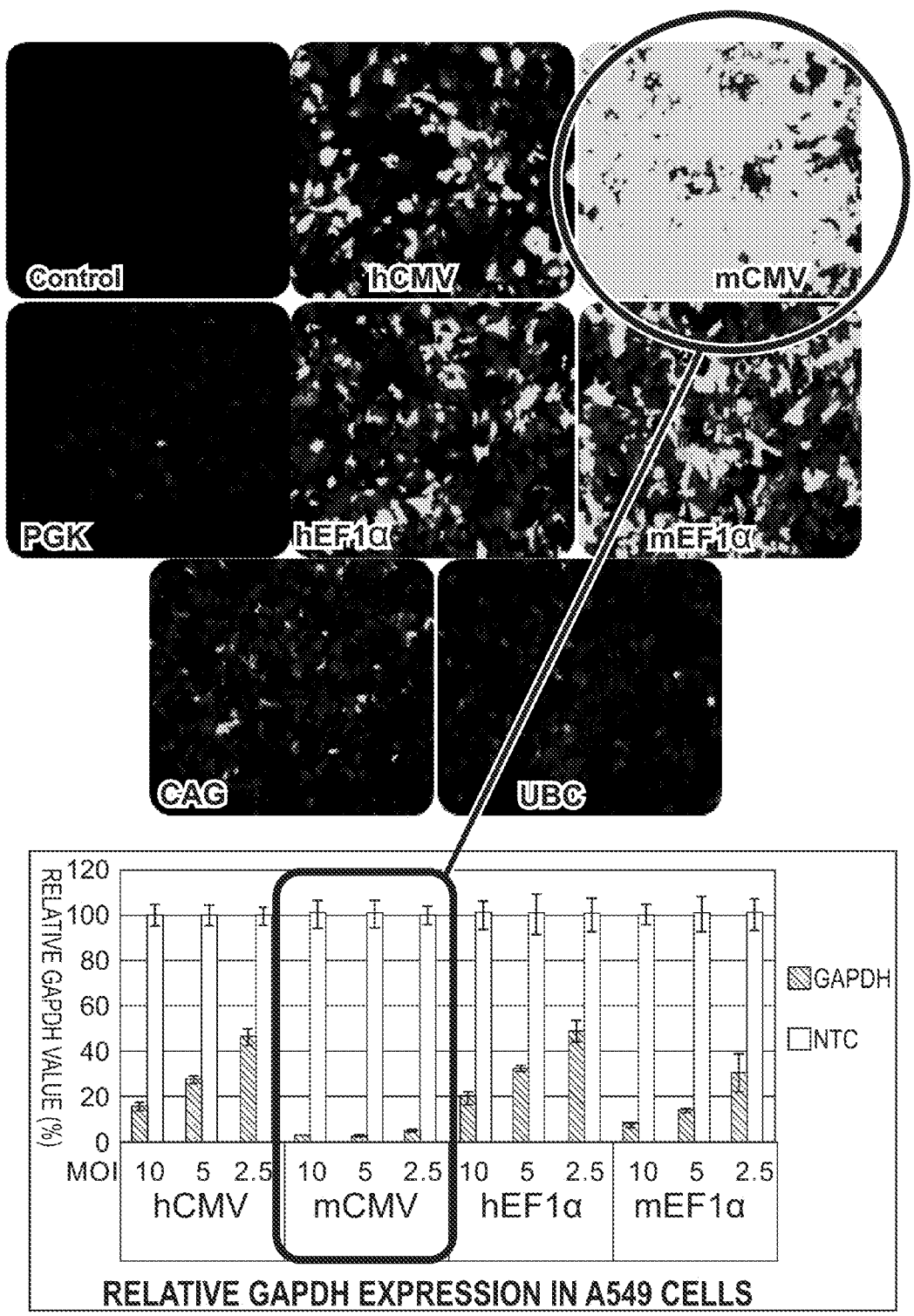
FIG. 6 is a representation of promoter activity as measured by GFP fluorescence from the results of example 3 in A549 cells and a measure of relative GAPDH expression following expression from four different promoters of an shRNA targeting GAPDH.

FIG. 6 (top) shows the greatest fluorescence with the mouse CMV promoter. FIG. 6 (bottom) shows a bar graph that contains the result of an experiment conducted under the following conditions:
Cell density: 7,000 per well in a 96-well plate.
MOI 10, 5, or 2.5 as indicated.
Time point of observation: 72 hours.
Assay: solaris QPCR.
Gene targeted: GAPDH.
Normalization method: based on 18S expression.
QPCR conditions: based on solaris protocol: 95 C, 10 min, followed by 40 cycles of, 15 seconds and 60 C, 60 seconds.

As with example 3, the qualitative assessment of the most active promoter as evidenced by GFP expression correlates with the quantitative measurement of housekeeping gene knockdown. Thus, FIG. 5 and FIG. 6 show how promoter activity and consequently the level of shRNA expression have a significant impact on the level of knockdown.

Example 5

Promoter Selection Plates

The arrayed SMARTchoice Promoter Selection Plate consists of lentiviral vector particles produced from SMARTchoice vectors co-expressing TurboGFP, a puromycin resistance selectable marker, and the Non-Targeting Control (NTC) shRNA in the context of the SMARTvector 2.0 miRNA scaffold. Two-fold serial dilutions of viral particles from the seven different promoters are arrayed in a 96-well plate as depicted in FIG. 7, with each row containing the indicated promoter:
Row A. Empty wells
Row B. hCMV—human cytomegalovirus intermediate early promoter
Row C. mCMV—mouse cytomegalovirus intermediate early promoter
Row D. hEF1α—human elongation factor 1 alpha promoter
Row E. mEF1α—mouse elongation factor 1 alpha promoter
Row F. CAG—chicken beta actin hybrid promoter
Row G. mPGK—mouse phosphoglycerate promoter
Row H. UBC—human ubiquitin C promoter
The activity of each promoter is evaluated by simply measuring the fluorescence intensity of TurboGFP expression following transduction of the cell of interest.

Figure 8C:
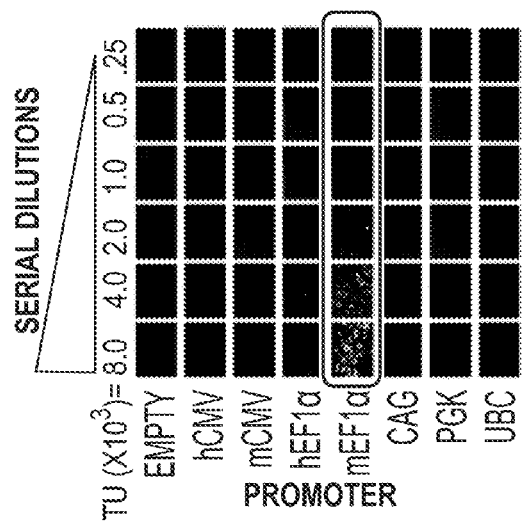
FIG. 8 is a representation of the GFP fluorescence intensities from the results in example 5 in A549 cells, HEK293T cells, and Jurkat cells following transduction with serial dilutions of test vectors in a plate according to an embodiment of the present invention.
Figure 8B:
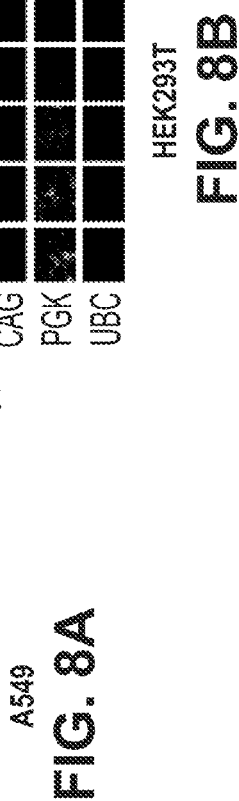
Figure 8A:
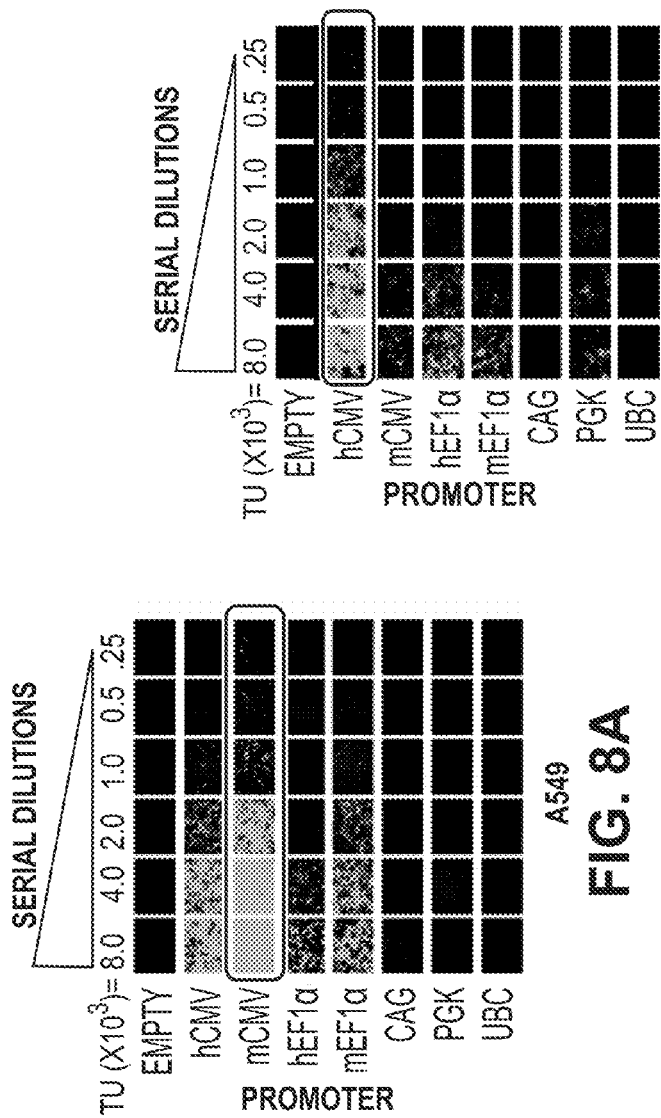

Three human cell lines, A549, HEK293T, and Jurkat cells, were transduced with lentiviral vector particles using the SMARTchoice Promoter Selection Plate. TurboGFP expression was assessed by fluorescent microscopy 72 hours post-transduction. As shown in FIG. 8, images clearly demonstrate that mCMV is the most functional promoter in A549 cells, hCMV is most active in HEK293T, and mEF1c is the strongest promoter tested in Jurkat cells. The results show that a promoter selection plate allows for rapid, qualitative assessment and identification of active promoters in cells of interest including cells that are difficult to transfect.

Example 6

Knockdown of shRNA Transduced Cells

Figure 9:
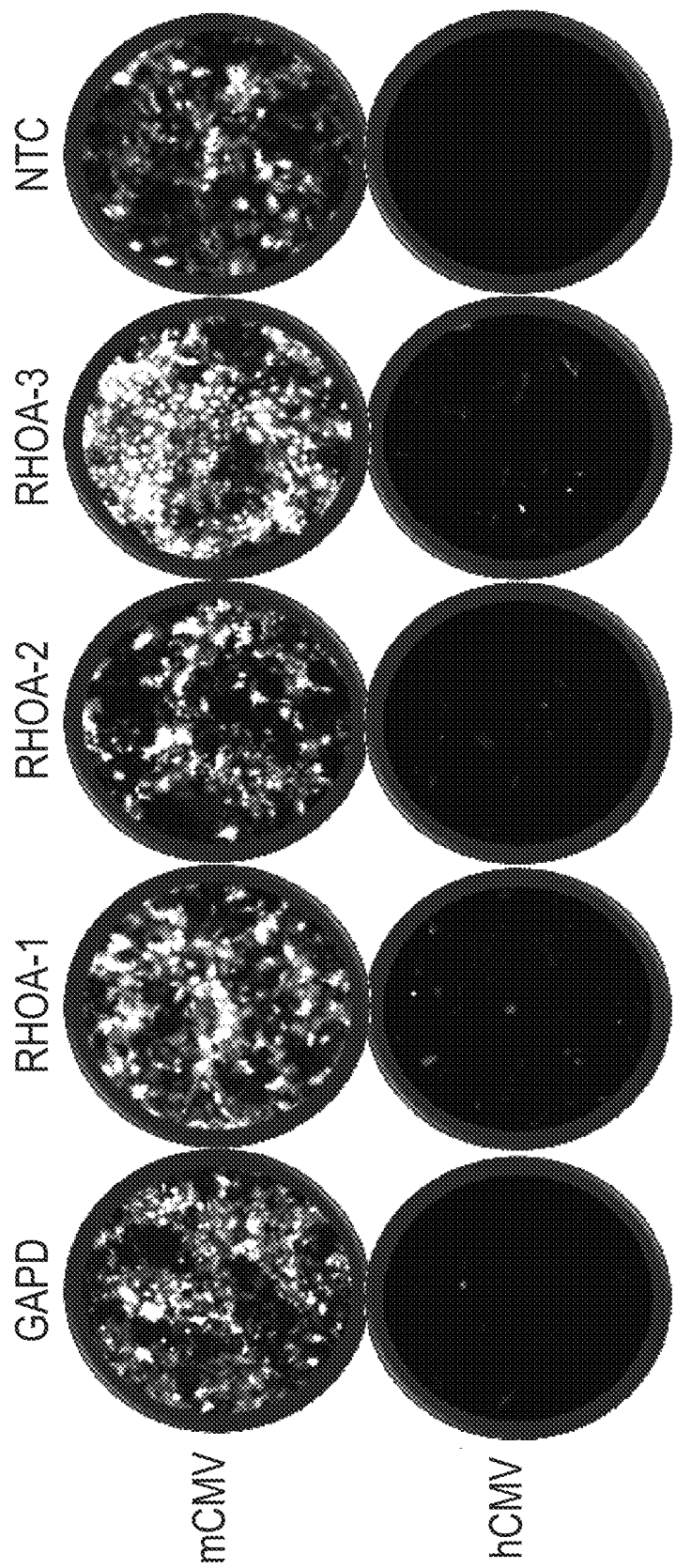
FIG. 9 is a representation of the GFP fluorescence intensities in A549 cells following transduction of test vectors in a plate according to an embodiment of the present invention.

Another experiment was run using a promoter selection plate in which the following promoters were used: human CMV and mouse CMV. As shown in FIG. 9, fluorescence was measured in A549 cells at 72 hours, with an MOI of 10. Fluorescence was consistently greater for the mouse CMV promoter is all systems: GAPD, RHOA-1, RHOA-2, RHOA-3 and NTC (non-targeting control).

Figure 10:
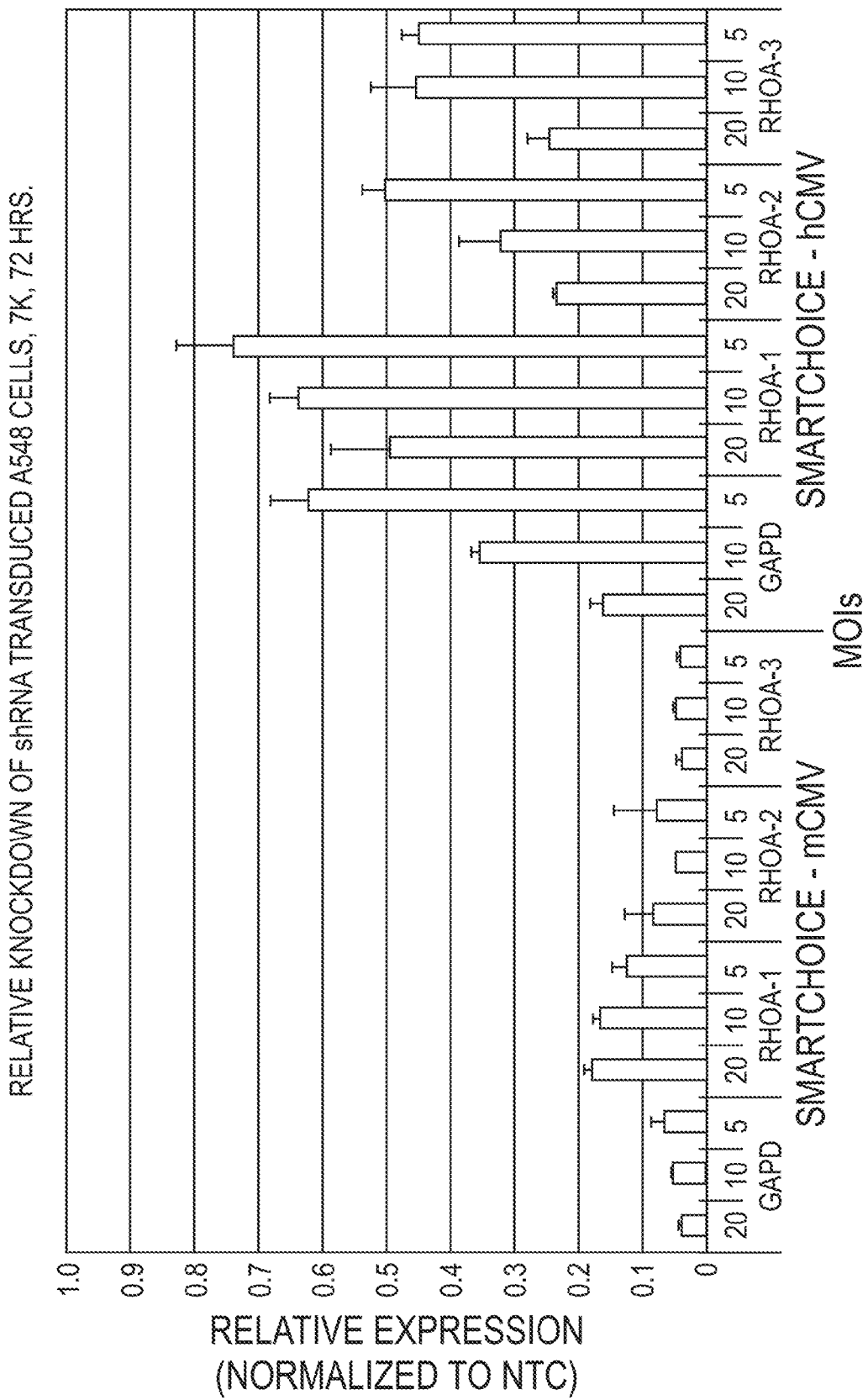
FIG. 10 is a representation of a quantitative analysis of gene silencing with three shRNAs targeting the RHOA gene and expressed by the mouse CMV and human CMV promoters in A549 cells.

FIG. 10 shows a quantitative analysis of relative expression in each of the systems as normalized relative to the control. The expression in systems using the mouse CMV vectors was greatly reduced relative to when using the human CMV vectors, which is consistent with the fluorescence results. Thus, an shRNA that previously showed poor functionality can be highly efficacious when driven by a more appropriate promoter.

Example 7

Figure 11:
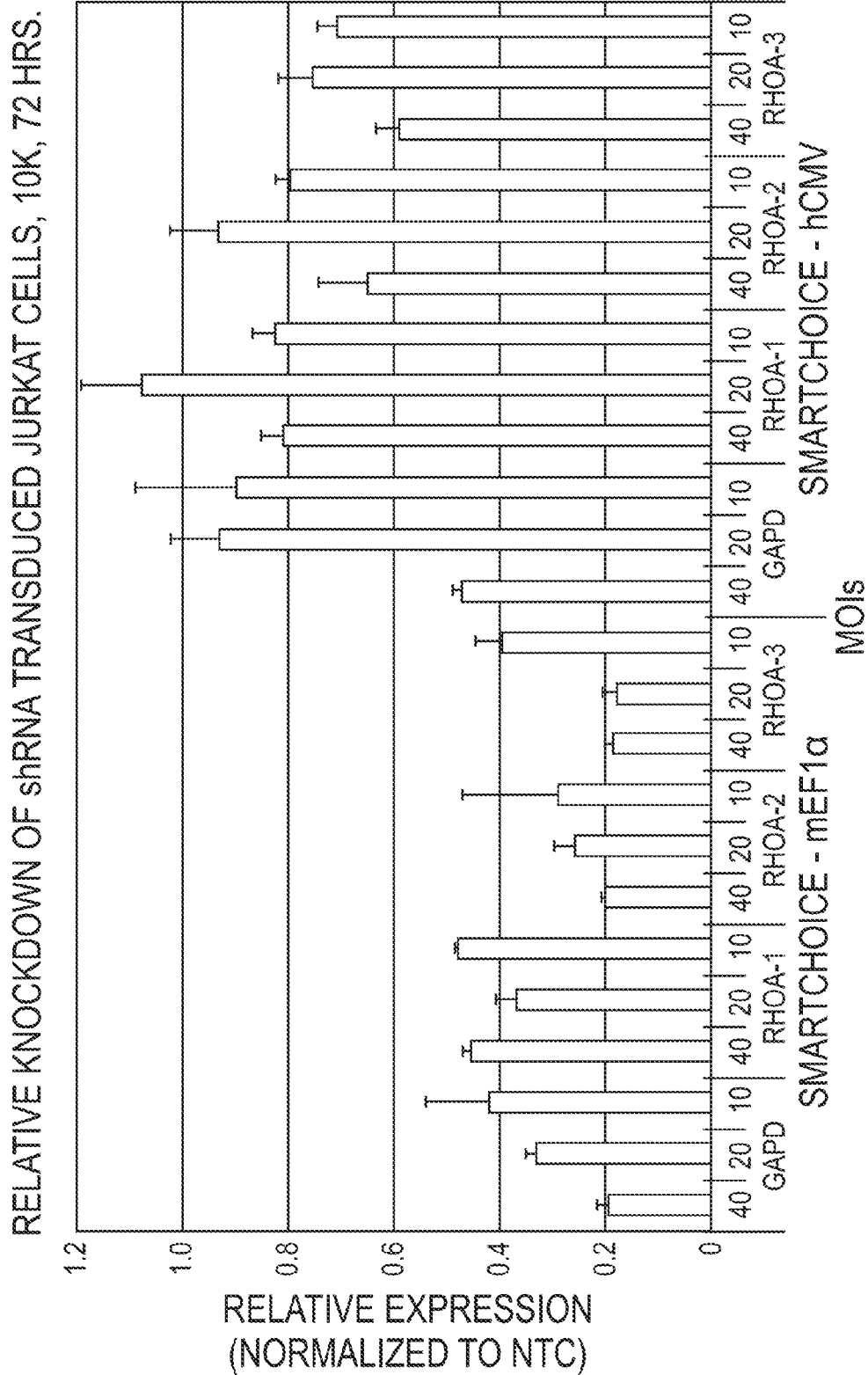
FIG. 11 is a representation of a quantitative analysis of gene silencing with three shRNAs targeting the RHOA gene and expressed by the mouse EF1α and human CMV promoters in Jurkat cells.

Cells that have Previously been Shown to be Difficult to Induce Effective Knockdown with shRNA-Containing Lentiviral Vectors An experiment was run in which Jurkat cells, which are known to be not only difficult to transfect, but also difficult to transduce were used. FIG. 11 shows a quantitative measure of the relative expression of shRNA normalized to a non-targeting control. This figure shows that none of the three shRNAs targeting RHOA in Jurkat cells were functional (knockdown greater than 70%) when expression was driven by the human CMV promoter, whereas two of the three shRNAs expressed by the mouse EF1α promoter knocked down gene target gene expression by greater than 80%.

Examples of promoter sequences hCMV promoter
(SEQ ID NO: 1)
aatagtaatcaattacggggtcattagttcatagcccatatatggagtt
ccgcgttacataacttacggtaaatggcccgcctggctgaccgcccaac
gacccccgcccattgacgtcaataatgacgtatgttcccatagtaacgc
caatagggactttccattgacgtcaatgggtggagtatttacggtaaac
tgcccacttggcagtacatcaagtgtatcatatgccaagtacgcccct
attgacgtcaatgacggtaaatggcccgcctggcattatgcccagtaca
tgaccttatgggactttcctacttggcagtacatctacgtattagtcat
cgctattaccatggtgatgcggttttggcagtacatcaatgggcgtgga
tagcggtttgactcacggggatttccaagtctccaccccattgacgtca
atgggagtttgttttggcaccaaaatcaacgggactttccaaaatgtcg
taacaactccgccccattgacgcaaatgggcggtaggcgtgtacggtgg
gaggtctatataagcagagctcgtttagtgaaccgtcagatc mCMV promoter
(SEQ ID NO: 2)
tggcacgtatactgagtcattagggactttccaatgggttttgcccagt
acataaggtcaataggggtgaatcaacaggaaagtcccattggagccaa
gtacactgagtcaataggggactttccattgggttttgcccagtacaaaa
ggtcaataggggggtgagtcaatgggttttcccattattggcacgtaca
taaggtcaataggggtgagtcattgggttttttccagccaatttaattaa
aacgccatgtactttccaccattgacgtcaatgggctattgaaactaa
tgcaacgtgaccttttaaacggtactttcccatagctgattaatgggaaa
gtaccgttctcagagccaatacacgtcaatgggaagtgaaagggcagcc
aaaacgtaacaccgccccggttttccctggaaattccatattggcacg
cattctattggctgagctgcgttctacgtgggtataagaggcgcgacca
gcgtcggtaccgtcgcagtcttcggtctgaccaccgtagaacgcaga hEF1α promoter
(SEQ ID NO: 3)
tccccgagaagttggggggaggggtcggcaattgaaccggtgcctagag
aaggtggcgcggggtaaactgggaaagtgatgtcgtgtactggctccgc
cttttttcccgagggtggggagaaccgtatataagtgcagtagtcgccg
tgaacgttcttttttcgcaacgggtttgccgccagaacacaggtaagtgc
cgtgtgtggttcccgcgggctggcctctttacgggttatggccttgc
gtgccttgaattacttccacctggctccagtacgtgattcttgatccg
agctggagccaggggcgggccttgcgctttaggagccccttcgcctcgt
gcttgagttgaggcctggcctgggcgctggggccgccgcgtgcgaatct ggtggcaccttcgcgcctgtctcgctgctttcgataagtctctagccat
ttaaaattttttgatgacctgctgcgacgcttttttttctggcaagatagt
cttgtaaatgcgggccaggatctgcacactggtatttcggttttttgggg
ccgcgggcggcgacggggcccgtgcgtcccagcgcacatgttcggcgag
gcggggcctgcgagcgcggccaccgagaatcggacggggtagtctcaa
gctggccggcctgctctggtgcctggcctcgcgccgccgtgtatcgccc
cgccctgggcggcaaggctggcccggtcggcaccagttgcgtgagcgga
aagatggccgcttcccggccctgctccaggggggctcaaaatggaggacg
cggcgctcgggagagcgggcgggtgagtcacccacacaaaggaaagggg
cctttccgtcctcagccgtcgcttcatgtgactccacggagtaccgggc
gccgtccaggcacctcgattagttctggagcttttggagtacgtcgtct
ttaggttgggggggagggtttttatgcgatggagtttccccacactgagt
gggtggagactgaagttaggccagcttggcacttgatgtaattctcctt
ggaatttgcccttttttgagtttggatcttggttcattctcaagcctcag
acagtggttcaaagttttttttcttccattcaggtgtcgt mEF1α promoter
(SEQ ID NO: 4)
agagtaattcatacaaaaggagggatcgccttcgcctggggaagtccca
gggaccgtcgctaaattctcataacccataatcccggtacccgccccac
cacagtgcgaggagcatgcgctcagggctgagcgcggggagagcagagc
acacaagctcatagaccctggtcgtgggggggagggcgcactgagcggg
gggggggggggtgatgggggggaggaccggggagctggcgcggggcaaa
ctgggaaagcggtgtcgtgtgctggctccgccctcttcccgagggtggg
ggagaacggtatataagtgcggcagtcgccttggacgttcttttttcgca
acgggtttgccgtcagaacgcaggtgaggggcgggtgtggcttccgcgg
gccgccgagctggaggtcctgctccgagcgggccgggccccgctgtcgt
cggcggggattagctgcgagcattcccgcttcgagttgcgggcggcgcg
ggaggcagagtgcgaggcctagcggcaacccgtagcctcgcctcgtgt
ccggcttgaggcctagcgtggtgtccgcgccgccgccgcgtgctactcc
ggccgcactctggtctttttttttttgttgttgttgttgccctgctgcc
ttcgattgccgttcagcaataggggctaacaaagggagggtgcgggct
tgctcgcccggagccggagaggtcatggttggggaggaatggagggac
aggagtggcggctggggccccgcccgccttcggagcacatgtccgacgcc
acctggatggggcgaggcctgggttttttcccgaagcaaccaggctggg
gttagcgtgccgaggccatgtggccccagcacccggcacgatctggctt
ggcggcgccgcgttgccctgcctccctaactagggtgaggccatcccgt
ccggcaccagttgcgtgcgtgaaagatggccgctcccgggccctgttg
caaggagctcaaaatggaggacgcggcagcccggtggagcgggcgggtg
agtcacccacacaaaggaagagggcctggtccctcaccggctgctgctt
cctgtgaccccgtggtcctatcggccgcaatagtcacctcgggcttttg
agcacggctagtcgcggcgggggaggggatgtaatggcgttggagtttt
gttcacatttggtgggtggagactagtcaggccagcctggcgctggaag -continued tcattttttggaatttgtcccccttgagttttgagcggagctaattctcgg gcttcttagcggttcaaaggtatcttttaaacccttttttaggtgttgt gaaaaccaccgctaattcaaagcaa CAG promoter (SEQ ID NO: 5)

gacattgattattgactagttattaatagtaatcaattacggggtcatt agttcatagcccatatatggagttccgcgttacataacttacggtaaat ggcccgcctggctgaccgcccaacgacccccgcccattgacgtcaataa tgacgtatgttcccatagtaacgccaatagggactttccattgacgtca atgggtggactatttacggtaaactgcccacttggcagtacatcaagtg tatcatatgccaagtacgccccctattgacgtcaatgacggtaaatggc ccgcctggcattatgcccagtacatgaccttatgggactttcctacttg gcagtacatctacgtattagtcatcgctattaccatgggtcgaggtgag ccccacgttctgcttcactctccccatctcccccccctccccacccca attttgtatttatttattttttaattattttgtgcagcgatgggggcgg gggggggggggcgcgcgccaggcggggcggggcgggcgaggggcggg gcggggcgaggcggagaggtgcggcggcagccaatcagagcggcgcgct ccgaaagtttccttttatggcgaggcggcggcggcggcggccctataaa aagcgaagcgcgcggcgggcgggagtcgctgcgttgccttcgccccgtg ccccgctccgcgccgcctcgcgccgcccgccccggctctgactgaccgc gttactcccacaggtgagcgggcgggacggcccttctcctccgggctgt aattagcgcttggtttaatgacggctcgtttcttttctgtggctgcgtg aaagccttaaagggctccgggagggccctttgtgcgggggggagcggct cggggggtgcgtgcgtgtgtgtgcgtggggagcgccgcgtgcggccc gcgctgcccggcggctgtgagcgctgcgggcgcggcgcggggctttgtg cgctccgcgtgtgcgcgaggggagcgcggccggggcggtgccccgcgg tgcgggggggctgcgaggggaacaaaggctgcgtgcggggtgtgtgcgt ggggggtgagcagggggtgtgggcgcggcggtcgggctgtaacccccc cctgcaccccctccccgagttgctgagcacggcccggcttcggtgcg gggctccgtgcggggcgtggcgcggggctcgccgtgccgggcgggggt ggcggcaggtgggggtgccgggcgggcggggccgcctcgggccgggga gggctcgggggaggggcgcggcggccccgagcgccggcggctgtcgag gcgcggcgagccgcagccattgccttttatggtaatcgtgcgagagggc gcagggacttccttttgtcccaaatctggcggagccgaaatctgggaggc gccgccgcacccctctagcggggcgcgggcgaagcggtgcggcgccggc aggaaggaaatgggcggggagggccttcgtgcgtcgccgcgccgccgtc cccttctccatctccagcctcggggctgccgcaggggacggctgcctt cgggggggacggggcagggcggggtttcggcttctggcgtgtgaccggcg gctctagagcctctgctaaccatgttcatgccttcttctttttcctaca gctcctgggcaacgtgctggttgttgtgctgtctcatcattttggcaaa gaattacccgccgccaccatgg mPGK promoter (SEQ ID NO: 6)

caattctaccgggtaggggaggcgcttttcccaaggcagtctggagcat gcgctttagcagccccgctgggcacttggcgctacacaagtggcctctg gcctcgcacacattccacatccaccggtaggcgccaaccggctccgttc tttggtggccccttcgcgccaccttctactcctcccctagtcaggaagt tccccccgccccgcagctcgcgtcgtgcaggacgtgacaaatggaagt agcacgtctcactagtctcgtgcagatggacagcaccgctgagcaatgg aagcgggtaggcctttggggcagcggccaatagcagctttgctccttcg cttttctgggctcagaggctgggaaggggtgggtccggggggcgggctcag gggcgggctcaggggcggggcgggcgcccgaaggtcctccggaggcccg gcattctgcacgcttcaaaagcgcacgtctgccgcgctgttctcctctt cctcatctccgggcctttcgacctgcagcccaag UBC promoter (SEQ ID NO: 7)

ggcctccgcgccgggttttggcgcctcccgcggggcgcccccctcctcac ggcgagcgctgccacgtcagacgaagggcgcagcgagcgtcctgatcct tccgcccggacgctcaggacagcggcccgctgctcataagactcggcct tagaaccccagtatcagcagaaggacattttaggacgggacttgggtga ctctagggcactggttttctttccagagagcggaacaggcgaggaaaag tagtcccttctcggcgattctgcggagggatctccgtggggcggtgaac gccgatgattatataaggacgcgccgggtgtggcacagctagttccgtc gcagccgggatttgggtcgcggttcttgtttgtggatcgctgtgatcgt cacttggtgagtagcgggctgctgggctggccggggctttcgtggccgc cgggccgctcggtgggacggaagcgtgtggagagaccgccaagggctgt agtctgggtccgcgagcaaggttgccctgaactgggggttgggggagc gcagcaaaatggcggctgttcccgagtcttgaatggaagacgcttgtga ggcgggctgtgaggtcgttgaaacaaggtgggggcatggtgggcggca agaacccaaggtcttgaggccttcgctaatgcgggaaagctcttattcg ggtgagatgggctggggcaccatctggggaccctgacgtgaagtttgtc actgactggagaactcggtttgtcgtctgttgcggggcggcagttatg gcggtgccgttgggcagtgcacccgtacctttgggagcgcgcgccctcg tcgtgtcgtgacgtcaccgttctgttggcttataatgcagggtggggc cacctgccggtaggtgtgcggtaggcttttctccgtcgcaggacgcagg gttcgggcctagggtaggctctcctgaatcgacaggcgccggacctctg gtgaggggagggataagtgaggcgtcagtttcttttggtcggttttatgt acctatcttcttaagtagctgaagctccggttttgaactatgcgctcgg ggttggcgagtgtgttttgtgaagttttttaggcaccttttgaaatgta atcatttgggtcaatatgtaattttcagtgttagactagtaaattgtcc gctaaattctggccgttttttggcttttttgttagac

I claim:

1. A plate for selection of a promoter sequence, wherein the plate comprises a first row of a plurality of loci and a second row of a plurality of loci, wherein at least two of the plurality of loci within the first row each comprise a first lentiviral vector comprising:
   (a) a promoter sequence selected from the group consisting of sequences for human CMV, mouse CMV, human EF1α, mouse EF1α, CAG, mouse PGK, and UBC; and
   (b) a reporter sequence; and
at least two of the plurality of loci within the second row each comprise a second lentiviral vector, wherein the second lentiviral vector is the same as the first lentiviral vector except that it comprises a different promoter sequence selected from the group consisting of sequences for human CMV, mouse CMV, human EF1α, mouse EF1α, CAG, mouse PGK, and UBC, wherein the at least two of the plurality of loci within the first row comprise a first locus and a second locus, wherein the amount of the first lentiviral vector in the first locus in the first row is from 2 fold to 6 fold the amount of the first lentiviral vector in the second locus in the first row, and the at least two of the plurality of loci in the second row comprise a first locus and a second locus, wherein the amount of the second lentiviral vector in the first locus in the second row is from 2 fold to 6 fold the amount of the second lentiviral vector in the second locus in the second row and wherein the first locus in the first row and the first locus in the second row are in a first column and the second locus in the first row and the second locus in the second row are in a second column.

2. The plate of claim 1, wherein the first lentiviral vector further comprises:
(a) an miRNA scaffolding sequence, wherein said miRNA scaffolding sequence is derived from an endogenous pri-miRNA sequence.

3. The plate of claim 2, wherein the first lentiviral vector further comprises:
(a) a mature strand insert sequence; and
(b) a star strand insert sequence, wherein said mature strand insert sequence and said star strand insert sequence are each 18-23 nucleotides in length, and said mature strand insert sequence and said star strand insert sequence are each located within the miRNA scaffolding sequence and the mature strand insert sequence is at least 60% complementary to the star strand insert sequence, and neither the mature strand insert sequence nor the star strand insert sequence comprise a sequence derived from an endogenous miRNA that comprises the pri-miRNA scaffolding.

4. A plate according to claim 3, wherein the mature strand insert sequence is a non-targeting control sequence.

5. A plate according to claim 1 further comprising a third row of a plurality of loci, wherein each of at least two of the plurality of loci within the third row comprises a third lentiviral vector that is the same as the first lentiviral vector, except that it contains a promoter sequence selected from the group consisting of sequences for human CMV, mouse CMV, human EF1α, mouse EF1α, CAG, mouse PGK, and UBC that is different from the promoter sequences of the first lentiviral vector and of the second lentiviral vector, wherein the at least two of the plurality of loci within the third row comprise a first locus and a second locus, wherein the amount of the third lentiviral vector in the first locus in the third row is from 2 fold to 6 fold the amount of the third lentiviral vector in the second locus in the first row, and wherein the first locus in the third row is in the first column and the second locus in the third row is in the second column.

6. A plate according to claim 5 further comprising a fourth row of a plurality of loci, wherein each of at least two of the plurality of loci within the fourth row comprises a fourth lentiviral vector that is the same as the first lentiviral vector, except that it contains a promoter sequence selected from the group consisting of sequences for human CMV, mouse CMV, human EF1α, mouse EF1α, CAG, mouse PGK, and UBC that is different from the promoter sequences of the first lentiviral vector, of the second lentiviral vector and of the third lentiviral vector, wherein the at least two of the plurality of loci in the fourth row comprise a first locus and a second locus, wherein the amount of the fourth lentiviral vector in the first locus in the fourth row is from 2 fold to 6 fold the amount of the fourth lentiviral vector in the second locus in the fourth row, and wherein the first locus in the fourth row is in the first column and the second locus in the fourth row is in the second column.

7. A plate according to claim 6 further comprising a fifth row of a plurality of loci, wherein each of at least two of the plurality of loci within the fifth row comprises a fifth lentiviral vector that is the same as the first lentiviral vector, except that it contains a promoter sequence selected from the group consisting of sequences for human CMV, mouse CMV, human EF1α, mouse EF1α, CAG, mouse PGK, and UBC that is different from the promoter sequences of the first lentiviral vector, of the second lentiviral vector, of the third lentiviral vector and of the fourth lentiviral vector, wherein the at least two of the plurality of loci in the fifth row comprise a first locus and a second locus, wherein the amount of the fifth lentiviral vector in the first locus in the fifth row is from 2 fold to 6 fold the amount of the fifth lentiviral vector in the second locus in the fifth row, and wherein the first locus in the fifth row is in the first column and the second locus in the fifth row is in the second column.

8. A plate according to claim 7 further comprising a sixth row of a plurality of loci, wherein at least two of the plurality of loci within the sixth row comprises a sixth lentiviral vector that is the same as the first lentiviral vector, except that it contains a promoter sequence selected from the group consisting of sequences for human CMV, mouse CMV, human EF1α, mouse EF1α, CAG, mouse PGK, and UBC that is different from the promoter sequence of the first lentiviral vector, of the second lentiviral vector, of the third lentiviral vector, of the fourth lentiviral vector and of the fifth lentiviral vector, wherein the at least two of the plurality of loci within the sixth row comprise a first locus and a second locus, wherein the amount of the sixth lentiviral vector in the first locus in the sixth row is from 2 fold to 6 fold the amount of the sixth lentiviral vector in the second locus in the sixth row, and wherein the first locus in the sixth row is in the first column and the second locus in the sixth row is in the second column.

9. The plate according to claim 1, wherein the first row further comprises a third locus, wherein the third locus of the first row comprises the first lentiviral vector and the amount of the first lentiviral vector in the second locus of the first row is from 2 fold to 6 fold the amount of the first lentiviral vector in the third locus of the first row, and the second row further comprises a third locus, wherein the third locus of the second row comprises the second lentiviral vector and the amount of the second lentiviral vector in the second locus of the second row is from 2 fold to 6 fold the amount of the second lentiviral vector in the third locus of the second row, and wherein the third locus of the first row and the third locus of the second row are in a third column.

10. The plate according to claim 9, wherein the first row further comprises a fourth locus, wherein the fourth locus of the first row comprises the first lentiviral vector and the amount of the first lentiviral vector in the third locus of the first row is from 2 fold to 6 fold the amount of the first lentiviral vector in the fourth locus of the first row, and the second row further comprises a fourth locus, wherein the fourth locus of the second row comprises the second lentiviral vector and the amount of the second lentiviral vector in the third locus of the second row is from 2 fold to 6 fold the amount of the second lentiviral vector in the fourth locus of the second row, and wherein the fourth locus of the first row and the fourth locus of the second row are in a fourth column.

11. The plate according to claim 10, wherein the first row further comprises a fifth locus, wherein the fifth locus of the first row comprises the first lentiviral vector and the amount of the first lentiviral vector in the fourth locus of the first row is from 2 fold to 6 fold the amount of the first lentiviral vector at the fifth locus of the first row, and the second row further comprises a fifth locus, wherein the fifth locus of the second row comprises the second lentiviral vector and the amount of the second lentiviral vector in the fourth locus of the second row is from 2 fold to 6 fold the amount of the second lentiviral vector in the fifth locus of the second row, and wherein the fifth locus of the first row and the fifth locus of the second row are in a fifth column.

12. The plate according to claim 11, wherein the first row further comprises a sixth locus, wherein the sixth locus of the first row comprises the first lentiviral vector and the amount of the first lentiviral vector in the fifth locus of the first row is from 2 fold to 6 fold the amount of the first lentiviral vector at the sixth locus of the first row, and the second row further comprises a sixth locus, wherein the sixth locus of the second row comprises the second lentiviral vector and the amount of the second lentiviral vector in the fifth locus of the second row is from 2 fold to 6 fold the amount of the second lentiviral vector at the sixth locus of the second row, and wherein the sixth locus of the first row and the sixth locus of the second row are in a sixth column.

13. The plate according to claim 12, wherein each of the first row and the second row further comprises:
- a seventh locus, wherein in the seventh locus is a lentiviral vector, wherein the identity and the amount of lentiviral vector in the seventh locus is the same as the identity and the amount of lentiviral vector in the first locus;
- an eighth locus, wherein in the eighth locus is a lentiviral vector, wherein the identity and the amount of lentiviral vector in the eighth locus is the same as the identity and the amount of lentiviral vector in the second locus;
- a ninth locus, wherein in the ninth locus is a lentiviral vector, wherein the identity and the amount of lentiviral vector in the ninth locus is the same as the identity and the amount of lentiviral vector in the third locus;
- a tenth locus, wherein in the tenth locus is a lentiviral vector, wherein the identity and the amount of lentiviral vector in the tenth locus is the same as the identity and the amount of lentiviral vector in the third locus;
- an eleventh locus, wherein in the eleventh locus is a lentiviral vector, wherein the identity and the amount of lentiviral vector in the eleventh locus is the same as the identity and the amount of lentiviral vector in the fifth locus;
- a twelfth locus, wherein in the twelfth locus is a lentiviral vector, wherein the identity and the amount of lentiviral vector in the twelfth locus is the same as the identity and the amount of lentiviral vector in the sixth locus;

wherein within each row, the first locus, the second locus, the third locus, the fourth locus, the fifth locus, the sixth locus, the seventh locus, the eighth locus, the ninth locus, the tenth locus, the eleventh locus and the twelfth locus are consecutive.

14. The plate according to claim 12, wherein: within the first row, there is a multiplicity of infection in the first locus, the second locus, the third locus, the fourth locus, the fifth locus and the sixth locus of 80, 40, 20, 10, 5 and 2.5, respectively; and within the second row, there is a multiplicity of infection in the first locus, the second locus, the third locus, the fourth locus, the fifth locus and the sixth locus of 80, 40, 20, 10, 5 and 2.5, respectively.

15. The plate according to claim 9 further comprising a control row, wherein all loci within the control row have an absence of lentiviral vectors.

* * * * *